US008093217B2

(12) United States Patent
Toole et al.

(10) Patent No.: US 8,093,217 B2
(45) Date of Patent: Jan. 10, 2012

(54) METHODS AND COMPOSITIONS FOR INHIBITION OF MULTI-DRUG RESISTANCE BY HYALURONAN OLIGOMERS

(75) Inventors: Bryan P. Toole, Mt. Pleasant, SC (US); Suniti Misra, Mount Pleasant, SC (US); Shibnath Ghatak, Mount Pleasant, SC (US)

(73) Assignee: Tufts University, Boston, MA (US)

( * ) Notice: Subject to any disclaimer, the term of this patent is extended or adjusted under 35 U.S.C. 154(b) by 798 days.

(21) Appl. No.: 10/835,511

(22) Filed: Apr. 29, 2004

(65) Prior Publication Data

US 2004/0229843 A1 Nov. 18, 2004

Related U.S. Application Data

(63) Continuation-in-part of application No. PCT/US03/20918, filed on Jul. 1, 2003.

(60) Provisional application No. 60/392,905, filed on Jul. 1, 2002, provisional application No. 60/453,761, filed on Mar. 11, 2003.

(51) Int. Cl.
*A01N 61/00* (2006.01)
*A61K 31/00* (2006.01)
*A61K 38/00* (2006.01)

(52) U.S. Cl. ............. 514/19.3; 514/1; 514/1.1; 514/1.3; 514/2.4; 514/2.6; 514/18.9; 514/19.2

(58) Field of Classification Search ............... 514/1, 1.1, 514/1.3, 2.4, 2.6, 18.9, 19.2, 19.3
See application file for complete search history.

(56) References Cited

U.S. PATENT DOCUMENTS

| 5,902,795 | A | 5/1999 | Toole et al. | |
|---|---|---|---|---|
| 5,976,874 | A * | 11/1999 | Altman et al. | ............. 435/320.1 |
| 2002/0131995 | A1 * | 9/2002 | Szoka, Jr. | ............. 424/450 |
| 2003/0026801 | A1 * | 2/2003 | Weiner et al. | ............. 424/144.1 |

FOREIGN PATENT DOCUMENTS

| CA | 2122519 A1 | 10/1995 |
|---|---|---|
| EP | 03742415 | 8/2004 |
| WO | WO 00/41730 | 7/2000 |
| WO | WO 01/39815 | 7/2001 |
| WO | WO 02/05852 A1 | 1/2002 |

OTHER PUBLICATIONS

Pumphrey et al. Neogylcans, carbodiimide-modified glycosaminoglycans: a new class of anticancer agents that inhibit cancer cell proliferation and induce apoptosis. Cancer Research 62: 3722-3728, Jul. 1, 2002.*
Peters et al. Population density and growth rate in laboratory mice. Laboratory Animals 24: 273-279, 1990.*
Ahrens et al. *Oncogene*, 20:3399-3408 (2001).
Almeida et al. *J. Cell Biol.*, 149:741-754 (2000).
Ballangrud et al. *Clin. Cancer Res.*, 5(10):3171s-3176s (1999).
Banerji et al. *J. Cell Biol.*, 144(4):789-801 (1999).
Bartolazzi et al. *J. Exp. Med.*, 180:53-66 (1994).
Batist, et al. *J. Biol. Chem.*, 261(33):15544-15549 (1986).
Baumgartner et al. *Cancer Lett.*, 131:85-99 (1998).
Biswas, *Cancer Lett.*, 24(2):201-207 (1984).
Biswas et al. *Cancer Res.*, 55(2):434-439 (1995).
Bono et al. *Mol. Biol. Cell*, 12:891-900 (2001).
Cantley et al. *Proc. Natl. Acad. Sci. USA*, 96: 4240-4245 (1999).
Ciardiello et al. *Int. J. Cancer*, 98:463-469 (2002).
Danen et al. *J. Cell Physiol.*, 189:1-13 (2001).
Datta et al. *Genes Dev.*, 13:2905-2927 (1999).
Denizot et al. *J. Immunol. Methods*, 89(2):271-277 (1986).
Desoize et al. *Crit. Rev. Oncol/Hematol.*, 36:193-207 (2000).
dit Faute et al. *Clin. Exp. Metastasis*, 19(2):161-168 (2002).
Evanko et al. *Arterioscler. Thromb. Vasc. Biol.*, 19:1004-1013 (1999).
Fairchild et al. *Cancer Res.*, 47(19):5141-5148 (1987).
Freedman et al. *Cell*, 3(4):355-359 (1974).
Frisch et al. *Curr. Opin. Cell Biol.*, 13:555-562 (2001).
Fu et al. *Eur. J. Cancer*, 38:418-426 (2002).
Ghatak et al. *J. Biol. Chem.*, 277(41):38013-38020 (2002).
Gottesman et al. *Nature Rev. Cancer*, 2:48-58 (2002).
Itano et al. *Cancer Res.*, 59:2499-2504 (1999).
Katso et al. *Annu. Rev. Cell Dev. Biol.*, 17:615-675 (2001).
Kosaki et al. *Cancer Res.*, 59:1141-1145 (1999).
Kuo et al. *Oncogene*, 21:1945-1954 (2002).
Kuo et al. *Bioconj. Chem.*, 2(4):232-241 (1991).
Lesley et al. *J. Biol. Chem.*, 275(35):26967-26975 (2000).
Liu et al. *Cancer Res.*, 61:5207-5214 (2001).
Liu et al. *Cancer Res.*, 61:1022-1028 (2001).
Mabuchi et al. *J. Biol. Chem.*, 277(36):33490-33500 (2002).
MacPherson et al. *J. Med. Microbiol.*, 2(2):161-165 (1969).
Makin et al. *Trends Cell Biol.*, 11(11):S22-S26 (2001).
Mason et al. *Biomaterials*, 21:31-36 (2000).
McGahon et al. *Methods Cell Biol.*, 46:153-185 (1995).
Misra et al. *J. Biol. Chem.*, 273(41):26638-26644 (1998).
Mohapatra et al. *J. Exp. Med.*, 183:1663-1668 (1996).
Noble, P.W., *Matrix Biol.*, 21:25-29 (2002).
O'Gorman et al. *Leuk. Res.*, 25:801-811 (2001).
Orford et al. *J. Cell Biol.*, 146(4):855-867 (1999).
Peterson et al. *Am. J. Pathol.*, 156(6):2159-2167 (2000).
Pouyani et al. *Bioconj. Chem.*, 5(4):339-347 (1994).

(Continued)

*Primary Examiner* — Alana H Dent
(74) *Attorney, Agent, or Firm* — Lawson & Weitzen, LLP; Sonia K. Guterman; Michael I. Falkoff

(57) ABSTRACT

Pharmaceutical compositions and methods for sensitizing multi-drug resistant cancer or radiation resistant cancer cells to chemotherapeutic agents are provided. Compositions include ligands of hyaluronan receptors, including glycosaminoglycans such as hyaluronan oligomers and derivatives of these oligomers, hyaluronan binding proteins, antibodies specific for hyaluronan receptors, hyaluronan mimetics, inhibitors of hyaluronan synthesis, and stimulators of hyaluronan degradation.

22 Claims, 22 Drawing Sheets

OTHER PUBLICATIONS

Prestwich et al. *J. Controlled Release*, 53(1-3):93-103 (1998).
Roskelley et al. *Semin. Cancer Biol.*, 12:97-104 (2002).
Sheng et al. *J. Biol. Chem.*, 276(17)14498-14504 (2001).
St. Croix et al. *J. Natl. Cancer Inst.*, 88(18): 1285-1296 (1996).
St Croix et al. *Cancer Lett.*, 131:35-44 (1998).
Šuša et al. *J. Biol. Chem.*, 267(32):22951-22956 (1992).
Termeer et al. *J. Exp. Med.*, 195(1):99-111 (2002).
Toole, B.P. *Glycobiol.*, 12(3):37R-42R (2002).
Toole et al. *Am. J. Pathol.*, 161(3):745-747 (2002).
Toole et al. *J. Biol. Chem.*, 277(7):4593-4596 (2002).
Turley et al. *J. Biol. Chem.*, 277(7):4589-4592 (2002).
Underhill et al. *J. Biol. Chem.*, 258(13):8086-8091 (1983).
Volk et al. *Cancer Res.*, 60:3514-3521 (2000).
Weigel et al. *J. Biol. Chem.*, 272(22)13997-14000 (1997).
Weigel et al. *BBRC*, 294(4):918-922 (2002).
Worm et al. *J. Biol. Chem.*, 276(43):39990-40000 (2001).
Yang et al. *Biochem. Pharmacol.*, 63:959-966 (2002).
Yeo et al. *Am. J. Pathol.*, 148(6):1733-1740 (1996).
Yoshida et al. *J. Biol. Chem.*, 275(1):497-506 (2000).
Zahalka et al. *J. Immunol.*, 154(10):5345-5355 (1995).
Zeng et al. *Int. J. Cancer*, 77:396-401 (1998).
Ziebell et al. *Chem. Biol.*, 8(11):1081-1094 (2001).
International Search Report for PCT/US03/20918, mailed Nov. 20, 2003.

\* cited by examiner 1 2 3 4 5 6

METHODS AND COMPOSITIONS FOR INHIBITION OF MULTI-DRUG RESISTANCE BY HYALURONAN OLIGOMERS

RELATED APPLICATIONS

This application claims the benefit of PCT application PCT/US03/20918 having a filing date of 1 Jul. 2003, and which claims priority to U.S. provisional application Ser. No. 60/392,905 filed Jul. 1, 2002, and U.S. provisional application Ser. No. 60/453,761 filed Mar. 11, 2003, each of which is hereby incorporated herein by reference in its entirety.

GOVERNMENT FUNDING

This invention was made in part with government support under grant CA73839 awarded by the National Institutes of Health. The government has certain rights in the invention.

TECHNICAL FIELD

The present invention relates to compositions and methods for inhibiting multi-drug resistance of cancer cells.

BACKGROUND

Drug resistance of cancer cells has frustrated many avenues of chemotherapy. An important component of all tissues is the extracellular matrix. This matrix provides structural integrity to tissues and organs and support to individual cells and groups of cells. In recent years it has become evident that extracellular matrix components also influence cell behavior in a profound manner. Of particular interest is their capacity to "normalize" cells in adult tissues, i.e. restrain cells from undergoing inappropriate proliferation or movement. On the other hand, other combinations of extracellular matrix molecules can promote dynamic cell behavior during embryonic development, wound healing, etc. Thus it is becoming apparent that extracellular matrix often provides the "context" for proper cell behavior under a particular circumstance.

Recent investigations have highlighted the importance of normal cell-extracellular matrix interactions in suppressing malignant behavior, and the potential role of aberrant cell-matrix interactions in the onset and progression of malignant characteristics. Hyaluronan (also known as hyaluronic acid or HA), a ubiquitous large extracellular polysaccharide, is a component of extracellular matrix that has been implicated in tumor progression.

SUMMARY

The invention in one aspect features a pharmaceutical composition for treating a multi-drug resistant cell. The composition includes a competitor of HA interactions (CHI) that occur in vivo, for example, the CHI is an HA receptor ligand, or is a decoy capable of binding HA. The invention provides the CHI in an effective dose for reducing resistance of the cell to a drug.

A "hyaluronan receptor ligand" is defined herein as an agent that binds to a hyaluronan receptor in a tissue. The agent can be a glycosaminoglycan, a small molecule, or an antibody. An example of a suitable glycosaminoglycan is an oligomer of HA, which competes with endogenous HA polymer for receptor binding. An example of a decoy capable of binding HA is an HA binding protein (HABP), which binds to HA in vivo thereby reducing the level of endogenous HA that can interact with endogenous HA receptors. Examples of HABP are soluble recombinant HA receptors, which can be genetically engineered from genes encoding HA receptors by standard methods. Alternatively, HABP can be engineered binding proteins from synthetic sources, or can be engineered from proteins unrelated to HA receptors. Such soluble HABP such as recombinant receptor proteins can be used to confer susceptibility to a multi-drug resistant cell in vivo, which following administration to the cell can serve as HA decoys by binding endogenous HA, thereby competing with endogenous receptors, and reducing transmission of signals from those receptors by the pathways as shown herein following administration of HA oligomers.

Another example of a CHI is an agent that reduces or inhibits expression of a receptor that binds HA, for example, an siRNA molecule that reduces expression of CD44. Yet other examples include without limitation HA mimetics, inhibitors of HA synthesis, and stimulators of HA degradation.

HA is endogenously produced as large polymers of a disaccharide subunit consisting of glucuronic acid and N-acetylglucosamine. A suitable HA oligomer, which is commercially available as described herein, contains at least three of these disaccharide subunits, for example, contains at least six disaccharide subunits. As HA polymers do not function to reduce resistance of multi-drug resistant cells to anti-cancer drugs, the oligomer contains less than 5,000 disaccharide subunits, for example, less than 750 disaccharide subunits, and even less than 200 disaccharide subunits.

To produce a product having an extended half-life in vivo as an administered therapeutic agent, or to provide some other advantageous property, the HA oligomer can be derivatized. As with any carbohydrate polymer, derivatized HA oligomer can be prepared from HA derivatives which have been, for example, alkylated, alkoxylated, and reduced. Further, HA can be oligomerized (for example, by digestion with hyaluronidase) first and then derivatized, or can be derivatized and then digested.

Derivatized HAs have been demonstrated for a number of different substituents: carbodiimide (Kuo, J. et al., 1991 Bioconj Chem 2(4);232-41); N-(2-hydroxypropyl)methacrylamide (Luo et al., 2002 Pharm Res 19(4):396-402); an amine-like functionality from which covalent attachment of steroidal and nonsteroidal anti-inflammatory drugs can be attached (Pouyani, T. et al. 1994 Bioconj Chem 5(4):339-47); hydrazide modification of carboxylic acid moieties of HA (Prestwhich et al. 1998 J Control Release 53: 93-103); and surfaces of polypropylene, polystyrene, and polytetrafluoroethylene (Mason et al. 2000 Biomaterials 21: 3106).

The multi-drug resistant cell can be a cancer cell or a bacterial cell. Thus the at least one drug to which the cell has become resistant generally is an anti-cancer agent. It is shown herein that the effective dose increases sensitivity of the cell to the drug by 40% to 90% compared to sensitivity of a control cell absent the ligand, for example, by at least 90%, for example, the effective dose increases sensitivity of the cell to the drug by 90% to 95%, or by 90% to 99% compared to sensitivity of a control cell absent the ligand.

In a particularly useful embodiment, the composition which improves susceptibility of the cell to the anti-cancer and also contain the anti-cancer agent. Alternatively, the composition can contain an additional therapeutic agent. The additional therapeutic agent is selected from the group of agents consisting of a: an anxiolytic, an anti-emetic, an anti-fatigue, a cytokine, an anti-hypertensive, and an anti-infective. Alternatively, the additional therapeutic agent is a hematopoietic or erythropoietic agent, for example, the agent is erythropoietin.

Further, the additional therapeutic agent can be an inhibitor of multi-drug resistance, for example, which is not a ligand of an HA receptor. The inhibitor is, for example, a verapamil, a cyclosporin A, a cyclosporin D, a reserpine analog, a trifluroperazine, a tamoxifen, a verapamil R isomer, a SDZ PSC-833, an MS-209, an S-9788, a GF120918, and a LY3335979.

Exemplary multi-drug resistant cancer cells include cells from cancer that originate in a melanoma; a colon carcinoma; a pancreatic cancer; a lymphoma; a leukemia; a brain tumor such as glioma; a lung cancer; an esophageal cancer; a mammary cancer; a prostate cancer; a head and neck cancer; an ovarian cancer; a kidney cancer; or a liver cancer.

In the embodiment in which the cell is bacterial, exemplary genera include: *Actinobacillus, Bacillus, Borrelia, Brucella, Campylobacter, Chlamydia, Clostridium, Coxiella, Enterococcus, Escherichia, Francisella, Hemophilus, Legionella, Mycobacterium, Neisseria, Pasteurella, Pneumophila, Pseudomonas, Rickettsia, Salmonella, Shigella, Staphylococcus, Streptococcus, Treponema*, and *Yersinia*.

The compositions described herein can be administered at an effective dose of at least 1 mg/kg body weight, for example, the effective dose is at least 5 mg/kg body weight, for example, the effective dose is at least 10 mg/kg body weight. In a preferred embodiment, the effective dose is 5 mg/kg body weight. The compositions can include a pharmaceutically acceptable excipient.

The composition which is an antibody binds with high specificity and affinity for an HA receptor can be specific for any of HA receptor, including without limitation, CD44, CD168 (RHAMM), HARE (Weigel et al. 2002 BBRC 294: 918-922), lyve-1 (Banerju et al. 1999 J Cell Biol 144: 789), layilin (Bono et al. 2001 Mol Cell Biol 12: 891), and Toll-4 (Termeer et al. 2002 J Exp Med 195: 99). Further, the genes encoding any of these or any other HA receptors can be genetically engineered to encode a soluble form of the receptor, which soluble form is an HABP that can serve as a competitor of HA interactions, specifically as a decoy that binds to HA and reduces the extent of interaction between HA and the endogenous membrane-bound forms of the receptor. Another type of HABP can be a naturally occurring protein, a derivative of a naturally occurring protein, or can be partially or entirely engineered and can be unrelated structurally to the receptor. The HABP binds HA, effectively competing with the receptor. HABPs that are not receptors or related to receptors include link proteins, brevican, neurocan, aggrecan, versican, TSG-6 (a TNF stimulated protein), and inter-alpha-trypsin inhibitor, which are generally secreted proteins. In addition, inhibition of expression of the receptor or down regulation, for example by use of siRNA encoding a complement of the mRNA for the receptor, is used to reverse drug resistance in a cell.

Other embodiments provided herein are products containing an hyaluronan receptor ligand and an anticancer agent as a combined preparations for simultaneous, separate, or sequential use in anti-cancer therapy; for example, products containing an hyaluronan oligomer preparation and at least one anticancer agent as a combined preparations for simultaneous, separate, or sequential use in anti-cancer therapy. In a related embodiment, the invention provides a combination of an hyaluronan receptor ligand and an anticancer agent; a combination of an hyaluronan olligomer and at least one anticancer agent; and either of these combinations formulated as a single composition; and either of these combinations formulated as separate compositions. The invention also provides a method of preparing a medicament for treating a patient having a cancer, comprising formulating the medicament to contain any of these combinations.

Another embodiment of the invention is a method for treating a multi-drug resistant cancer. The method includes contacting a cell that has acquired resistance to at least one anti-cancer agent with a composition comprising a competitor of hyaluronan interactions and the at least one anti-cancer agent, wherein the competitor confers sensitivity to the anti-cancer agent on the cell, thereby treating the cancer.

In a related embodiment, the invention provides a method of preparing a medicament for treating a multi-drug resistant cancer, the method involving formulating the medicament to include a competitor of hyaluronan interactions and the at least one anti-cancer agent, and contacting a cell that has acquired resistance to at least one anti-cancer agent with the medicament, wherein the competitor confers sensitivity to the anti-cancer agent on the cell, thereby treating the cancer.

Another method provided herein is for treating a radiation resistant cancer, the method comprising: contacting a cell that has acquired resistance to at least one source of anti-cancer radiation with a composition comprising a competitor of an HA interaction and the at least one source of anti-cancer radiation, wherein the competitor confers sensitivity to the anti-cancer agent on the cells, thereby treating the cancer. The cell can be a cancer cell in a subject. Further, the competitor is an HA oligomer. The method can further comprise evaluating progression of the cancer. The HA oligomer in any of these methods is administered in a dose effective to confer sensitivity of the cell to the anti-cancer agent and inhibit growth or viability of the cells. Further, contacting with the HA oligomer is administering to the subject an amount sufficient to induce programmed cell death.

In a related embodiment, the invention provides a method of preparing a medicament for treating a radiation-resistant cancer, the method involving formulating the medicament to include a competitor of hyaluronan interactions, and contacting a cell that has acquired resistance to at least one source of anti-cancer radiation with the medicament and the at least one source of anti-cancer radiation, wherein the competitor confers sensitivity to the anti-cancer radiation on the cell, thereby treating the cancer. The invention further provides any of these methods in which the cell is in a subject. The competitor of hyaluronan interaction is, for example, an hyaluronan oligomer. With any of these methods, a further step can involve evaluating progression of the cancer. Contacting the cell with the hyaluronan oligomer is administering a dose effective to confer sensitivity of the cell to the anti-cancer agent or the anti-cancer radiation and inhibit growth or viability of the cells. For example, the dose is an amount sufficient to induce programmed cell death or apoptosis.

Another method provided herein is treating a multidrug resistant cancer. In this method, a subject is administered a therapeutically effective dose of each of an anti-cancer agent and a competitor of hyaluronan interactions, such as an hyaluronan receptor ligand, such as hyaluronan oligomers. Another method provided herein is treating a multidrug resistant cancer comprising administering to a subject in need thereof a therapeutically effective dose of each of an anti-cancer agent and a CHI such as hyaluronan oligomer. The anti-cancer agent and the hyaluronan oligomer can be co-administered, or can be administered separately, for example, can be administered sequentially. The cancer is: melanoma; colon carcinoma; pancreatic cancer; lymphoma; leukemia; glioma; lung cancer; esophageal cancer; mammary cancer; prostate; head and neck cancer; ovarian cancer; kidney cancer; or liver cancer.

In yet another embodiment, the invention provides a method for preparing a medicament for treating a multidrug resistant cancer, the method involving formulating the medicament to include a therapeutically effective dose of each of an anti-cancer agent and a competitor of hyaluronan interactions. The anticancer agent and the competitor of hyaluronan interactions are, for example, co-administered. In an alternative embodiment of the method, the anticancer agent and the competitor of hyaluronan interactions are administered sequentially. The cancer is melanoma; colon carcinoma; pancreatic cancer; lymphoma; leukemia; glioma; lung cancer; esophageal cancer; mammary cancer; prostate; head and neck cancer; ovarian cancer; kidney cancer; or liver cancer.

Yet another embodiment provided herein is a method of evaluating a potential inhibitor of resistance of a cell to an anti-cancer agent. This method includes contacting a first sample of a cancer cell that has acquired resistance to the anti-cancer therapeutic agent; and contacting a second sample of the cell in the presence of the anti-cancer therapeutic and the potential agent, wherein a reduction of an extent of a cell viability parameter by the potential anti-cancer agent in the second sample, compared to the extent in the first sample, and to a third control sample of the cell grown in the absence of the anti-cancer agent, is an indication that the potential inhibitor is an effective composition for treating a cellular resistance to the anti-cancer agent. The cell viability parameter to be measured can be: tumor size in vivo, anchorage independent colony formation, anchorage dependent colony formation, cell macromolecular synthesis, cell number, programmed cell death, cellular caspase activity, cellular PI3 kinase activity, Akt phosphorylation, BAD phosphorylation, FKHR phosphorylation, Fas expression, and PTEN phosphatase activity.

An embodiment of the invention provides a kit for treating a multi-drug resistant cell, comprising an HA receptor ligand or an HA receptor decoy, a container, and instructions for use to treat the cell. The cell for example is a cancer cell or a bacterial cell. The kit further can include at least one anti-cancer agent, or at least one antibacterial agent. The ligand can be, for example, an HA oligomer, and the anti-cancer agent can be: γ-radiation, adriamycin, methotrexate, cisplatin, paclitaxel, doxorubicin, vinblastine, vincristine, BCNU (1,3-bis(2-chloroethyl)-1-nitrosourea), camptosar, 5-flurouracil, Gleevac, Velcade (PS-341), ZD0473, and oncovine. The instructions can include administering the HA oligomers to treat the cell in a subject.

Additional drugs that are suitable anti-cancer agents can be coadministered with the HA oligomer compositions as described herein, using the methods and kits herein. Such drugs include but are not limited to the following approved drugs: pamidronate (Aredia); anastrozole (Arimidex); exemestane (Aromasin); bleomycin (Blenoxane); irinotecan (Camptosar); leucovorin; daunorubicin; cytaravine (CepoCyt); epirubicin (Ellence); etopos09901 ide (Etopophos); toremifene (Fareston); letrozole (Femara); gemcitabine (Gemzar); imatinib (Gleevac); topotecan (Hycamtin); tamoxifen (Nolvadex); paclifaxel (Taxol); docetaxel (Taxotere); capecitabine (Xeloda); temoxolomide (Temodar); nitrosourea; procarbazine (Matulane); valrubicin (Valstar); and goserelin (Zoladex). Drugs currently in clinical trials such as Velcade (PS-341; bortezomid) can also be administered with HA oligomer compositions.

BRIEF DESCRIPTION OF THE DRAWINGS

FIG. 18 is a set of line graphs showing a resulting cell number, on the ordinate, following drug treatment with doxorubicin, concentration (log) in nM on the abscissa, showing restoration of drug sensitivity (inhibition of drug resistance) by HA oligomers, soluble hyaluronan-binding decoys, and CD44 siRNA, using derivatives of MCF-7 cells as in FIG. 17 above.

FIG. 20 is a set of bar graphs and a line graph showing that hyaluronan oligomers inhibit drug transport by promoting drug efflux in MCF-7 and MCH-7/Adr cells.

DETAILED DESCRIPTION OF SPECIFIC EMBODIMENTS

Figure 1A:
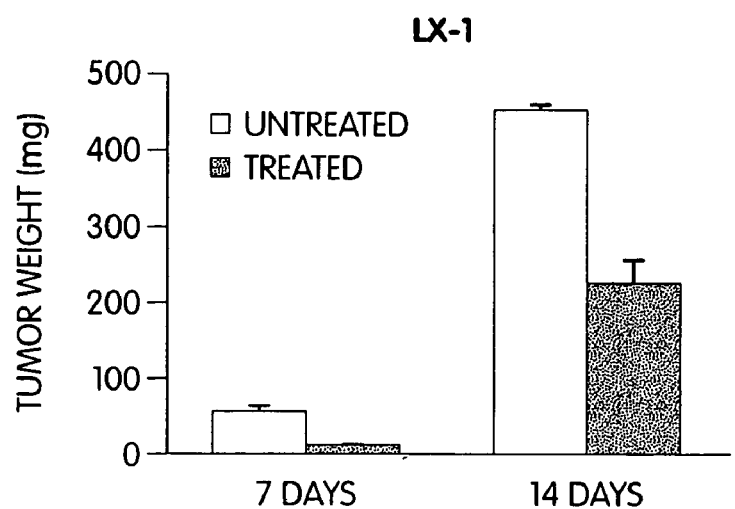
FIG. 1A is a bar graph showing inhibition of tumor growth in vivo by hyaluronan oligomers. LX-1 human lung carcinoma cells ($1.0 \times 10^6$ per animal for 7 day experiments; $0.5 \times 10^6$ for 14 days) were injected subcutaneously into nude mice. ALZET pumps (7-day or 14-day) containing 100 or 200 µl, respectively, of PBS alone or of 1 mg/ml hyaluronan oligomers dissolved in PBS were implanted at the injection sites. These pumps delivered the oligomers at a rate of ~0.5 µg/0.5 µl/hour. At the end of treatment for 7 or 14 days, the animals were euthanized with $CO_2$ and the tumors were weighed. Results are presented as an average of four independent experiments±S.D.

HA is a high molecular weight glycosaminoglycan (GAG) that is distributed ubiquitously in vertebrate tissues, and is expressed at elevated levels in many tumor types. In breast cancer cells, the level of hyaluronan concentration is a negative predictor of survival. HA-tumor cell interactions are shown herein to lead to enhanced activity of the phosphoinositide-3-kinase/Akt cell survival pathway and that small hyaluronan oligosaccharides antagonize endogenous hyaluronan polymer interactions, stimulating phosphatase and tensin (PTEN) expression and suppressing the cell survival pathway. Under anchorage-independent conditions, HA oligomers inhibit growth and induce apoptosis in cancer cells. HA oligomers may influence drug resistance by their effects both on the cell survival pathway and on ABC transporter function.

Experiments have demonstrated that HA oligomers diminish resistance of MDA-MB231 human breast cancer cells to methotrexate by two orders of magnitude. Whether HA oligomers reverse resistance to several drugs commonly used in treating cancer patients is of clinical importance is restoring susceptibility of cells to drugs to which the cells have become resistant in the course of a therapeutic treatment protocol.

Multi-drug resistant MCF-7/adrR human mammary carcinoma cells are used to determine whether HA oligomers sensitize these cells to treatment with doxorubicin, paclitaxel and vinblastine. These chemicals represent three classes of drugs that are commonly used for cancer patients and to which MCF-7/adrR cells are resistant. Resistance to apoptosis in monolayer culture and in spheroid culture, where resistance is often enhanced, is tested. In addition uptake and efflux of doxorubicin in MCF-7/adrR cells and of methotrexate in MB231 cells are measured to determine whether the oligomers affect drug accumulation. Finally, resistance of MCF-7/adrR cells to treatment with doxorubicin in the presence and absence of HA oligomers is tested in nude mice xenografts to ensure that results obtained in culture also apply in vivo.

Multi-drug resistance of cancer cells remains a serious problem in treatment today. Since HA oligomers are non-toxic and non-immunogenic, they may provide a novel avenue for improving the efficacy of chemotherapy in cancer patients. HA oligomers are shown herein to retard tumor growth in vivo. The possibility that these oligomers also reverse chemoresistance by increasing cell susceptibility to chemotherapeutic agents may lead to novel treatments that enhance current chemotherapeutic protocols.

Increased amounts of hyaluronan are shown herein to enhance tumor cell survival and suppress tumor cell death, thus promoting tumor growth and metastasis. Shorter lengths of an HA polymer (HA "oligomers") antagonize the effect of full-size, polymeric HA. HA oligomers have now been found to act by suppressing biochemical reactions that may be important in promoting multi-drug resistance to chemotherapy. Examples herein addressing the effect of HA oligomers on resistance of human breast cancer cells in cell culture to methotrexate, a commonly used chemotherapeutic agent, show that HA oligomers re-sensitize resistant cells to drug treatment. That this is the case with other chemotherapeutic drugs, and that HA oligomers sensitize resistant cells, is also shown herein.

HA expression enhances the activity of the PI3-kinase/Akt cell survival pathway. Small oligomers of HA are HA receptor ligands that antagonize the effect of endogenous HA polymer interactions by suppressing the PI3-kinase/Akt cell survival pathway and inducing apoptosis under anchorage-independent conditions. Examples herein further show that HA oligomers sensitize chemoresistant cancer cells by suppressing the cell survival pathway and sensitizing cells to apoptotic mechanisms.

Drug resistance in cancer cells, including multi-drug resistance, has been related to alterations in cell survival and apoptotic pathways, in particular the PI3-kinase/Akt pathway. HA oligomers are shown herein to suppress this pathway, and to sensitize cancer cells to chemotherapeutic drugs. HA and the Malignant Phenotype.

HA is a linear glycosaminoglycan composed of 2,000-25,000 disaccharides of glucuronic acid and N-acetylglucosamine: [β1,4-GlcUA-β1,3-GlcNAc—]$_n$, with molecular weights ranging from $10^5$ to $10^7$ daltons (Da). The disaccharide subunit has a molecular weight of 400 Da. Hyaluronan synthases (termed Has1, Has2, Has3) are integral plasma membrane proteins whose active sites are located at the intracellular face of the membrane (Weigel, P. H., et al. J Biol Chem, 272: 13997-14000, 1997). Newly synthesized HA is extruded directly onto the cell surface; it is either retained there by sustained attachment to the synthase or by interactions with receptors, or it is released into pericellular and extracellular matrices. Regulation of targeting to these various locations is not understood at this time.

HA has multiple physiological and cellular roles that arise from its unique biophysical and interactive properties (reviewed in Toole, B. P., et al. Cell Dev Biol, 12: 79-87, 2001; Toole, B. P., et al. Glycobiology, 12: 37R-42R, 2002). There are at least three ways in which HA can influence normal and abnormal cell behavior. First, due to its biophysical properties, free HA has a profound effect on the biomechanical properties of extracellular and pericellular matrices in which cells reside. Second, hyaluronan forms a repetitive template for specific interactions with other pericellular macromolecules, thus contributing to the assembly, structural integrity and physiological properties of these matrices: Thus, HA makes extracellular matrix more conducive to cell shape changes required for cell division and motility (Hall, C. L., et al. J Cell Biol, 126: 575-588, 1994; Evanko, S. P., et al. Arterioscler Thromb Vasc Biol, 19: 1004-1013, 1999). Third, HA interacts with cell surface receptors that transduce intracellular signals and influence cellular form and behavior directly (Turley, E. A., et al. J Biol Chem, 277: 4589-4592, 2002).

Experimental over-expression of the HA synthase, Has2, in HT1080 human fibrosarcoma cells gives rise to elevated hyaluronan production and causes increased tumor cell proliferation in vivo and under anchorage-independent conditions in vitro (Kosaki, R., et al. Cancer Res, 59: 1141-1145, 1999). Similar results were obtained in vivo on over-expression of Has3 in TSU human prostate tumor cells (Liu, N., et al. Cancer Res, 61: 5207-5214, 2001). In mouse mammary carcinoma cell lines selected for high and low HA production, decreased formation of metastatic nodules in the lung after intravenous injection occurred in lines selected for low HA production, and the metastatic potential of these cells was rescued by increasing HA production via transfection with Has1 (Itano, N., et al. Cancer Res, 59: 2499-2504, 1999).

Approaches used to perturb endogenous HA-protein interactions are: over-expressing soluble HA binding proteins (HABPs) to increase the amount of in vivo HA decoys; and administering HA receptor ligands such as HA oligosaccharides, and antibodies that block HA binding. Soluble HABPs competitively displace HA from its endogenous cell surface receptors, e.g. CD44 and CD168 (RHAMM), thus inhibiting putative downstream events. Several studies have demonstrated inhibition of tumor progression by treatment with soluble forms of CD44 (Sy, M. S., et al. J Exp Med, 176: 623-627, 1992; Bartolazzi, A. et al. J Exp Med, 180: 53-66, 1994). Over-expression of soluble CD44 in mouse mammary carcinoma cells or in human malignant melanoma cells leads to inhibition in vivo of growth, local invasion and metastasis (Yu, Q., et al. J Exp Med, 186: 1985-1996, 1997; Yu, Q. et al. Genes Dev, 13: 35-48, 1999; Peterson, R. M., et al. Am J Pathol, 156: 2159-2167, 2000; Ahrens, T., et al. Oncogene, 20: 3399-3408, 2001). No significant effects were obtained in these studies if the soluble CD44 was mutated such that HA binding was eliminated in the mutated CD44. Soluble CD168 (RHAMM), another HABP, also inhibits metastasis (Mohapatra, S., et al. J Exp Med, 183: 1663-1668, 1996) and a HA-binding complex derived from cartilage inhibits both tumor growth and metastasis (Liu, N., et al. Cancer Res, 61: 1022-1028, 2001). HA oligomers compete with endogenous polymeric hyaluronan-receptor interactions, thus resulting in low valency, low affinity binding rather than polyvalent, high affinity interactions with receptors (Underhill, C. B., et al. J Biol Chem, 258: 8086-8091, 1983).

Modes of systemic administration of the pharmaceutical compositions herein include, but are not limited to, transdermal, intramuscular, intraperitoneal, intravenous, subcutaneous, intranasal, and oral routes. The compounds may be administered by any convenient route, for example, by infusion or bolus injection, by absorption through epithelial or mucocutaneous linings (e.g., oral mucosa, rectal and intestinal mucosa, etc.), and may be administered together with other biologically active agents.

The present invention in another embodiment provides pharmaceutical compositions comprising a therapeutically effective amount of a competitor of HA interactions (CHI) such as an HA receptor ligand, alone or in conjunction with another agent, such as an anti-cancer agent. Further, a pharmaceutically acceptable carrier or excipient can be added. Such a carrier includes but is not limited to saline, buffered saline, dextrose, water, glycerol, ethanol, and combinations thereof. The formulation should suit the mode of administration.

The compositions herein can further comprise wetting or emulsifying agents, or pH buffering agents. The composition can be a liquid solution, suspension, emulsion, tablet, pill, capsule, sustained release formulation, or powder. The compositions can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Various delivery systems are known and can be used to administer a composition of the invention, e.g., encapsulation in liposomes, microparticles, microcapsules and the like.

Where necessary, the composition may also include a solubilizing agent and a local anesthetic to ameliorate pain at the site of the injection. Generally, the ingredients are supplied either separately or mixed together in unit dosage form, for example, as a dry, lyophilized powder or water-free concentrate in a hermetically sealed container such as an ampoule or sachette, for example, indicating the quantity of active agent. Where the composition is to be administered by infusion, it can be dispensed with an infusion bottle containing sterile pharmaceutical grade water, buffer, or saline. Where the composition is administered by injection, an ampoule of sterile water or saline for injection can be provided so that the ingredients may be mixed prior to administration.

The compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the CHI such as HABP, or HA receptor ligand, which is effective in the treatment of multi-drug resistance of an unwanted cell depends on the nature of the disorder or condition, and can be determined by standard clinical techniques. The precise dose to be employed in the formulation will also depend on the route of administration, and the seriousness of the disease or disorder, and should be decided according to the judgment of the practitioner and each patient's circumstances. Routine determinations of extent of resistance of the unwanted cell to the chemotherapeutic agent are determined by one of ordinary skill in the art. However the amount is also determined by route of administration, for example, suitable dosage ranges for subcutaneous administration are generally about 20-500 micrograms of an active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

The invention in other embodiments provides a pharmaceutical pack or kit comprising one or more containers filled with one or more of the ingredients of the pharmaceutical compositions of the invention. Associated with such container(s) can be various written materials such as instructions for use, or a notice in the form prescribed by a governmental agency regulating the manufacture, use or sale of pharmaceuticals or biological products, which notice reflects approval by the agency of manufacture, use or sale for human administration.

The invention in various embodiments now having been fully described, additional embodiments are exemplified by the following Examples and claims, which are not intended to be construed as further limiting. The contents of all cited references are hereby incorporated by reference herein.

EXAMPLES

The following materials and methods were used throughout the Examples herein.

Cells. LX-1 human lung carcinoma cells were obtained as described previously and re-passaged in nude mice before use. (Biswas, C. (1984) *Cancer Lett* 24, 201-207). HCT 116 cells were provided by Dr. B. Vogelstein, Johns Hopkins Medical School. TA3/St cells were obtained from Dr. H. F. Dvorak, Harvard Medical School, and maintained in our laboratory (Yeo, T. K., Nagy, J. A., Yeo, K. T., Dvorak, H. F., and Toole, B. P. (1996) *Am J Pathol* 148, 1733-1740). All cell lines were cultured in DMEM-high glucose medium without phenol red and containing 10% fetal bovine serum, penicillin/streptomycin and 1 mM glutamine (Life Technologies, Rockville, Md.). The cell lines were passaged every 3-4 days and maintained at 37° C. in 5% $CO_2$.

Material. Hyaluronan oligomers were fractionated from hyaluronidase digests of purified polymer by tangential flow filtration as described previously (Zeng, C., et al. (1998) *Int J Cancer* 77, 396-401) and were supplied by Anika Therapeutics Inc (Woburn, Mass.). Hyaluronan polymer, mol. wt. ~80 kDa and ~2,000 kDa, were gifts from Genzyme Inc and Anika Therapeutics Inc, respectively. Chitin oligomers were obtained from Seikagaku America (Falmouth, Mass.) and chondroitin sulfate from Sigma (St. Louis, Mo.). Non-adherent Ultra-low cluster plates (Costar 3471) were obtained from Corning Incorporated (Corning, N.Y.). ALZET pumps were from ALZA Corporation (Palo Alto, Calif.). [$\gamma$-$^{32}$P] ATP (6000 Ci/mmol) was purchased from NEN Life Science Products; DEVD-p-nitroanilide and all other reagents for the caspase-3 assay from Biovision Research Products (Mountain View, Calif.); reagents for SDS-polyacrylamide gel electrophoresis from Bio-Rad (Richmond, Calif.); enhanced chemiluminescence reagents from Amersham Pharmacia Biotech (Buckinghamshire, England); phospho-AKT pathway sampler kit from Cell Signaling Technology (Beverly, Mass.). Antibody against PTEN (A2B 1), antibodies against PI3 kinase isoforms and antibody against human CD44 (DF1485) were purchased from Santa Cruz Biotechnology (Santa Cruz, Calif.). Antibody against mouse CD44 (KM81) was from ATCC (Rockville, Md.). All other reagents were the highest grade from Sigma.

Tumor growth in vivo. The effect of hyaluronan oligomers on tumor growth in vivo was assessed in a similar manner to that described previously (Zeng, C., et al. (1998) *Int J Cancer* 77, 396-401). Five to six week-old nude mice (Balb/c nu/nu, male; Charles River Breeding Laboratories) or A/Jax mice (Jackson Laboratory, Bar Harbor, Me.) were used in groups of five mice per experimental point. ALZET osmotic pumps, containing PBS alone or hyaluronan oligomers dissolved in PBS, were inserted under the skin in the dorsal region of the mice by procedures recommended by ALZA scientific products and approved by the Animal Research Committee. On the day after implantation of the pump, $0.5$-$1.0 \times 10^5$-$10^6$ tumor cells in 0.1 ml PBS were injected immediately in front of the pump. Mice were euthanized by $CO_2$ after 7 or 14 day of treatment and growth was determined by weighing the tumor.

Anchorage-independent growth assay. A modification of previously published techniques was used (MacPherson, J., et al. (1969) *J Med Microbiol* 2, 161-165). The assay was done in six-well plates with a base layer containing 0.6% agar in DMEM, 10% fetal bovine serum (GIBCO), 1 mM glutamine, and 100 units penicillin plus 100 µg Streptomycin per ml. This layer was overlaid with a second layer of 1 ml 0.2% agar (containing 20% fetal bovine serum, 2 mM glutamine and 200 units penicillin plus 200 µg streptomycin) mixed with 1 ml of a suspension of 2500 cells, with or without addition of 100 µg/ml hyaluronan oligomers, in PBS. The plates were incubated at 37° C. for 10-14 days, and the diameter of tumor colonies was determined with a microscope equipped with an ocular scale in the eyepiece. Colonies with diameter greater than 0.2 mm were counted.

Treatment of Tumor Cells and Preparation of Cell Lysates for Biochemical Assays. TA3/St and HCT116 cells were grown for 72 hours in 14 cm culture dishes, then harvested by trypsinization, washed in PBS and suspended in DMEM containing 10% FBS. Two million cells from these cultures were added to each well of non-adherent, Ultra-low cluster plates and incubated in suspension at 37° C. for a further 72 hours. The cells from each well were then collected, washed in PBS, suspended in 5 ml DMEM medium containing 2% bovine serum albumin (Cohn Analog, Sigma), re-plated in the cluster plates, and incubated in suspension at 37° C. for 96 hours; similar results were obtained with pre-incubations of 24-96 hours for most measurements. The hyaluronan oligomers or other reagents were then added and the cells incubated for another 24 hours in suspension.

The cells treated as above were harvested by centrifugation at room temperature. The pellets were washed twice in PBS, then lysed in buffer containing 1% Nonidet P-40 and protease inhibitors. Cell lysis was achieved by vortexing for three cycles of 15 sec at high speed followed by cooling on ice. The lysate was centrifuged at 12,000×g for 15 min at 4° C. in an Eppendorf 5415R centrifuge. After measuring the protein content of the supernatant, it was flash-frozen in liquid nitrogen and stored at −80° C. until use in the assays below.

Apoptosis assay. TA3/St cells, grown as described in the section above were assayed as described elsewhere (McGabon, A. et al. Methods Cell Biol 46: 153-185, 1995). Briefly, 1 µl of dye mixture (acridine orange and ethidium bromide, 100 µg each in 1 ml) was mixed with 25 µl of cell suspension containing ~$5 \times 10^5$ cells per ml in medium. Ten µl of this suspension was placed on a clean slide and examined with a 40× objective using a fluorescent microscope with a blue filter. Viable cells (green) and apoptotic cells containing fragmented nuclei (red) were counted and the percentage of apoptotic cells was then calculated.

Caspase-3 assay. Two hundred µg of cell lysate protein were used for each assay. The assay was carried out following manufacturer's instructions (Biovision Research Products) and is based on spectrophotometric detection of the chromophore p-nitroanilide at 405 nm after cleavage from the labeled substrate, DEVD-p-nitroanilide.

PI3 kinase assay. For assay of total PI3 kinase, 250 ng of cell lysate protein were used per assay. Assays were performed in a 50 µl reaction mixture containing 0.001% Nonidet P-40, 150 µM ATP, 25 mM $MgC_2$, 5 mM EGTA, 150 µM ATP, 25 µCi of [$\gamma$-$^{32}$P] ATP, 125 mM MOPS, pH 7.0, and 0.2 mg/ml sonicated lipids containing phosphatidyl serine, phosphatidyl inositol and phosphatidyl inositol-4,5 bisphosphate in a 1:1:1 (v:v:v) ratio in sonication buffer (25 mM MOPS, pH 7.0, 1 mm EGTA) (Whitman, M. et al (1985) *Nature* 315, 239-242; Susa, M., et al. (1992) *J Biol Chem* 267, 22951-22956; Misra, S., et al. (1998) *J Biol Chem* 273, 26638-26644). The reactions were carried out at 37° C. for 20 min and stopped by addition of 100 µl of $CH_3OH$/1M HCl (1:1). Lipids were extracted twice with 100 µl of chloroform. The organic layers were combined, dried under nitrogen, and analyzed by thin layer chromatography. $^{32}$P-labeled phosphoinositides were resolved in water:acetic acid:n-propanol (34:1:65) and detected by autoradiography. $^{32}$P incorporation into phosphatidylinositol 3,4,5-phosphate ($PIP_3$) was quantified by liquid scintillation counting of thin layer chromatography spots scraped into and eluted in scintillation fluid.

For assay of specific PI3 kinase isoforms, whole cell lysates were incubated with antibody against the particular isoform plus protein A-Sepharose. PI3 kinase activity of the enzyme immobilized on beads was then measured as described above.

Immunoblotting. Cell lysate preparations were denatured at 65° C. for 5 min and loaded (15-30 µg protein per lane) onto a 10% polyacrylamide gel. Electrophoresis was performed on a Bio-Rad minigel apparatus. Proteins were transferred to nitrocellulose membranes and blocked for 1 h with Tris-buffered saline containing 5% nonfat dry milk and 0.1% Tween-20. Membranes were then washed and probed with the appropriate antibody diluted in Tris-buffered saline containing 5% bovine serum albumin (for polyclonal antibodies) or 5% nonfat dry milk (for monoclonal antibodies). The secondary antibodies used were anti-rabbit IgG (New England Bio-labs) and goat anti-mouse IgG (Bio-Rad), which were conjugated with horseradish peroxidase. Immunoreactive bands were detected by enhanced chemiluminescence and the sizes of proteins were estimated using prestained molecular weight standards. Immunoreactive bands were quantified by densitometry. Membranes were reused after neutralization with 15% $H_2O_2$ or stripping at 50° C. (according to manufacturers' procedures, Amersham, Pharmacia Biotech).

Example 1

Hyaluronan Oligomers Inhibit Tumor Growth In Vivo

Figure 1B:
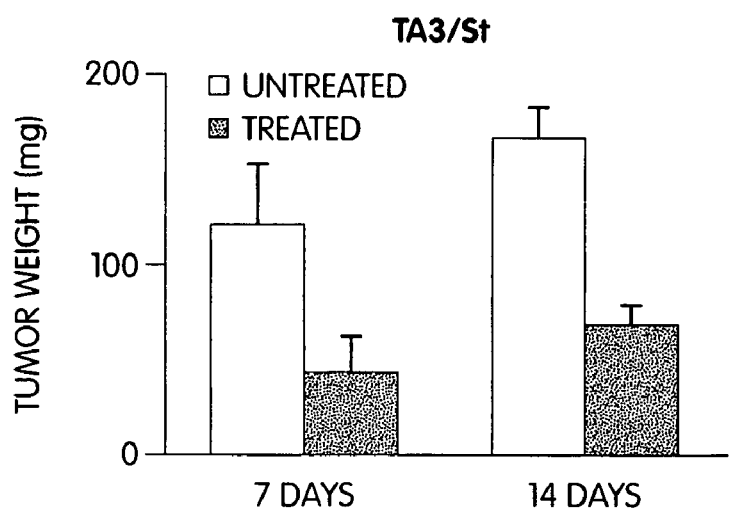
FIG. 1B is a bar graph showing inhibition of tumor growth in vivo by hyaluronan oligomers. TA3/St mouse mammary carcinoma cells (0.5 or $1.0 \times 10^6$, as for LX-1) were injected subcutaneously into syngeneic A/Jax mice, which were further treated as in FIG. 1A.

Administration of hyaluronan oligomers at the site of subcutaneous implantation of B16-F10 murine melanoma cells inhibits their growth by 50-85% depending on timing of exposure (Zeng, C., et al. (1998) *Int J Cancer* 77, 396-401). To determine whether or not this effect was applicable to other tumor cells, experiments we performed with LX-1 human lung carcinoma cells in nude mice and TA3/St murine mammary carcinoma cells in syngeneic mice. In each experiment, tumor cells were injected subcutaneously into groups of 5 control and 5 treated animals. The hyaluronan oligomers were administered from ALZET mini-osmotic pumps implanted adjacent to the site of injection one day prior to injection of tumor cells. The oligomers were delivered at a rate of ~0.5 µg/0.5 µl/h over the course of 7 or 14 days. Control animals received vehicle (PBS) only. The hyaluronan oligomers inhibited LX-1 tumor growth by ~50-80% (FIG. 1A) and TA3/St tumor growth by ~60-65% (FIG. 1B) over these time periods, i.e. to a similar degree to that found for B6-F10 cells.

In additional experiments, animals injected with LX-1 cells were left untreated for 7 days, and then treated with oligomers for 14 days; in two such experiments, inhibition of growth varied between 40 and 75%. When the opposite was done, i.e. treatment for 14 days followed by no treatment for 7 days, 68% inhibition was obtained. When treated for 7 days followed by no treatment for 14 days, 52% inhibition was obtained.

Example 2

Hyaluronan Oligomers Inhibit Anchorage-Independent Growth and Induce Apoptosis of Tumor Cells In monolayer cell culture, i.e. under anchorage-dependent conditions, hyaluronan oligomers at a concentration of 100-150 µg/ml were shown to have little effect on proliferation of B16-F10 murine melanoma, TA3/St murine mammary carcinoma, LX-1 human lung carcinoma, and HCT116 human colon carcinoma cells. This lack of inhibition of proliferation under standard conditions indicates that the hyaluronan oligomers are not toxic.

Figure 2:
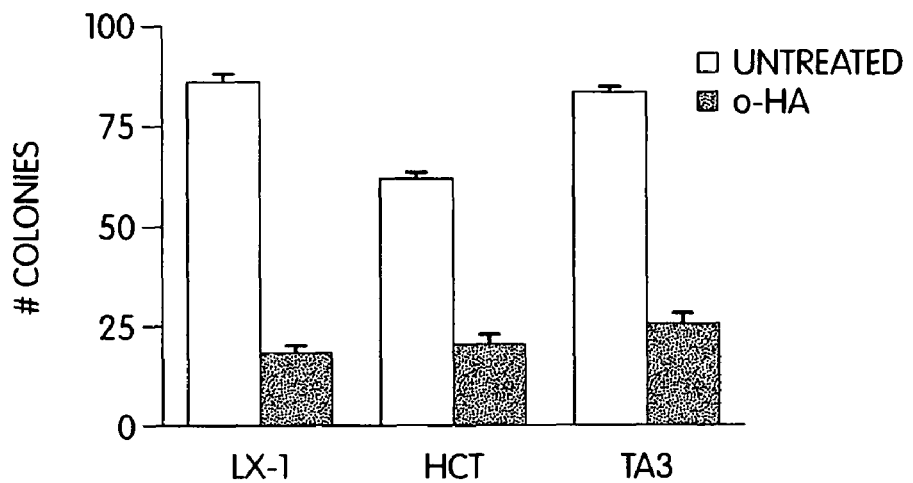
FIG. 2 is a bar graph showing inhibition of anchorage independent growth by hyaluronan oligomers. LX-1 human lung carcinoma, HCT116 human colon carcinoma or TA3/St murine mammary carcinoma cells, harvested from logarithmically growing cultures, were plated in soft agar at ~2,500 cells per well of 6-well plates in the presence or absence of 100 µg/ml of hyaluronan oligomers (o-HA). The cultures were incubated for 14 days at 37° C., and then the numbers of colonies >0.2 mm in size were counted. Results are expressed as an average of three independent experiments±S.D.

A hallmark characteristic of tumor cells, however, is their ability to grow in an anchorage-independent manner (Freedman, V. H., et al. (1974) *Cell* 3, 355-359). It is shown herein that hyaluronan oligomers decrease anchorage-independent growth of tumor cells, as assayed by their ability to grow as colonies in soft agar. Inclusion of 150 µg/ml hyaluronan oligomers in the soft agar assay inhibits colony formation by LX-1 human lung carcinoma, HCT116 human colon carcinoma, and TA3/St murine mammary carcinoma cells by 80, 68 and 72%, respectively (FIG. 2). Similar results have been obtained with several other tumor cell types, including human glioma and mammary carcinoma cells.

Figure 3:
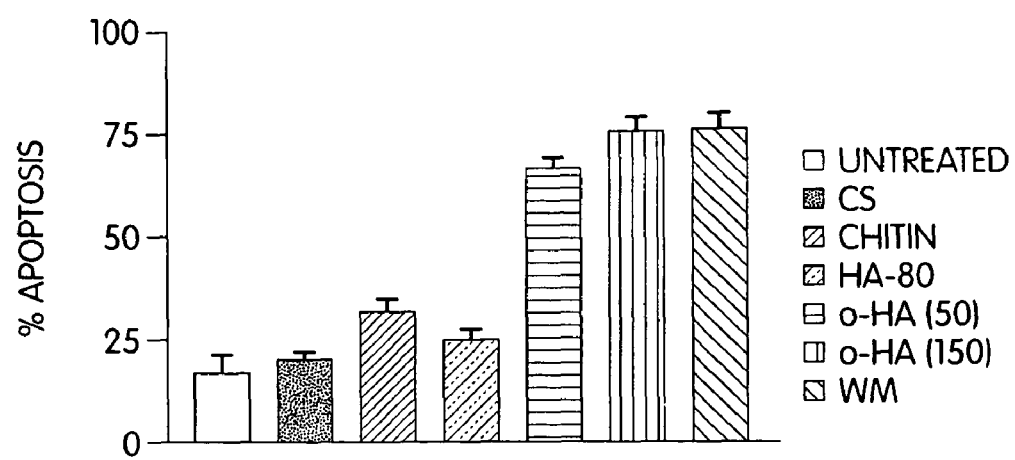
FIG. 3 is a bar graph showing induction of apoptosis by hyaluronan oligomers under anchorage-independent conditions. TA3/St murine mammary carcinoma cells were grown in suspension in serum-free medium for 24 hours in the presence of 50 or 150 µg/ml hyaluronan oligomers (o-HA), 150 µg/ml of ~80 kDa molecular weight hyaluronan polymer (HA-80), 150 µg/ml chitin oligomers, 150 µg/ml chondroitin sulfate (CS), or 50 nM wortmannin (WM), a specific inhibitor of mammalian PI3 kinase (phosphoinositide 3-kinase). Apoptotic cells were then analyzed and counted as described in the EXAMPLES section. Results represent the average of two experiments and are expressed as percentage of total cells±range.

Whether inhibition of anchorage-independent growth is due to induction of apoptosis was then tested. To do this, incubated TA3/St were cells in suspension, i.e. anchorage-independent conditions, in the presence or absence of hyaluronan oligomers. The level of apoptosis increased from ~13% in the absence of hyaluronan oligomers to 70-75% in the presence of 50-150 µg/ml oligomers (FIG. 3). Control untreated cells exhibited less than 25% apoptosis, hence the effect of the presence of HA oligomers observed herein is to increase in frequency of apoptosis by more than three-fold.

The effect also of various reagents related to hyaluronan oligomers was also tested. We used chitin oligomers as a negative control since they are similar to the hyaluronan oligomers in size and in chemical composition; they are sufficiently closely related that hyaluronan synthase can produce chitin oligomers (Yoshida, M., Itano, N., Yamada, Y., and Kimata, K. (2000) *J Biol Chem* 275, 497-506). They do not have a significant effect (FIG. 3). Hyaluronan polymer and chondroitin sulfate also do not have significant effects (FIG. 3). Survival of carcinoma cells under anchorage-independent conditions, as opposed to normal epithelia, is often attributed to elevated levels of the PI3 kinase/Akt pathway, so the effect of hyaluronan oligomers with that of wortmannin, an inhibitor of PI3 kinase was compared. The level of apoptosis induced by hyaluronan oligomers was equivalent to that caused by wortmannin (FIG. 3).

Figure 4A:
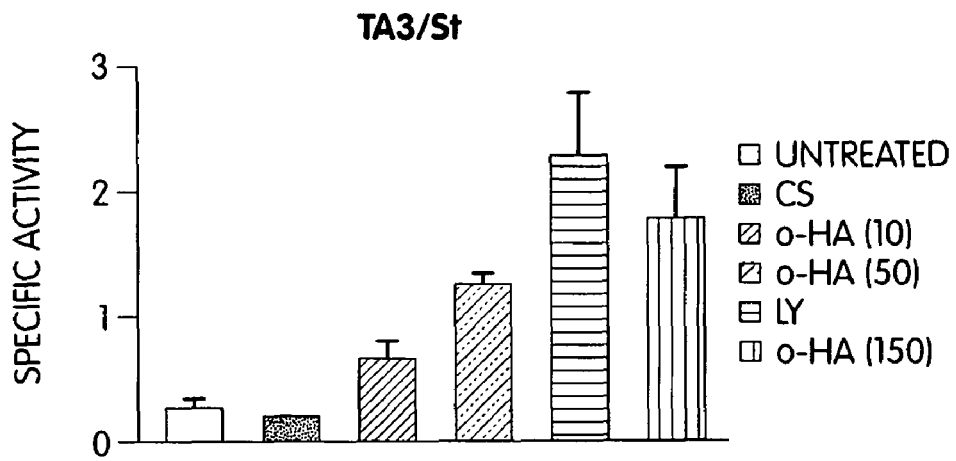
FIG. 4A is a bar graph showing stimulation of caspase-3 activity in TA3/St murine mammary carcinoma cells by hyaluronan oligomers. Cells were grown in suspension in serum-free medium for 24 hours in the presence of 10, 50 or 150 µg/ml hyaluronan oligomers (o-HA), 150 µg/ml chondroitin sulfate (CS), or 20 µM LY294002 (LY), a specific inhibitor of mammalian PI3 kinase, and then analyzed for caspase-3 activity. Results are presented as the mean of specific activity (absorbance at 405 nm/mg/90 min)±S.D. for three independent experiments.
Figure 4B:
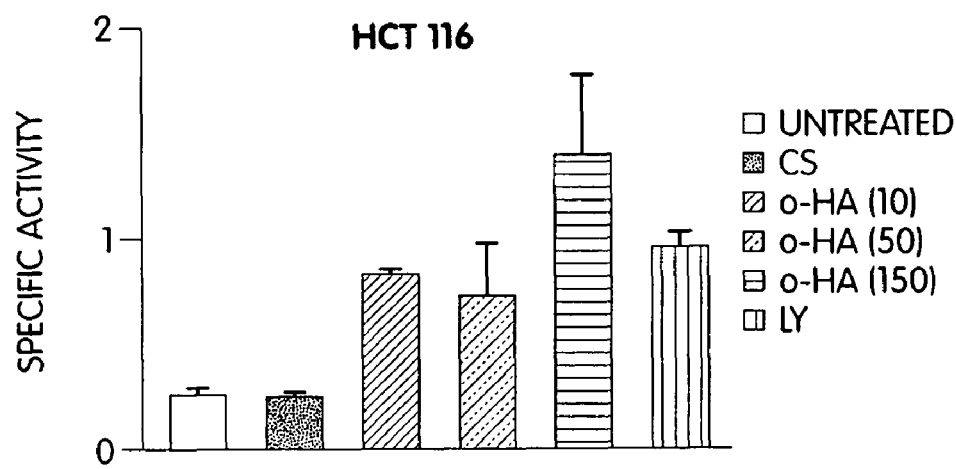
FIG. 4B shows measurements similar to those in FIG. 4A with HCT116 human colon carcinoma cells.

The effect of hyaluronan oligomers on caspase-3 activity was measured and data show that they stimulated caspase-3 activity by as much as 7 to 10-fold in TA3/St (FIG. 4A) and HCT116 cells (FIG. 4B). Chondroitin sulfate had no significant effect on caspase-3 activity in either cell type. As with the apoptosis assay, the effect of the hyaluronan oligomers was equal to or greater than that of inhibitors of PI3 kinase (FIG. 4A, 4B).

Example 3

Hyaluronan Oligomers Suppress the PI3 Kinase/Akt Cell Survival Pathway

The activity of the PI3 kinase/Akt cell survival pathway is elevated in many types of tumor cells (Cantley, L. C., et al. (1999) *Proc Natl Acad Sci USA* 96, 4240-4245; Katso, R., et al. (2001) *Annu Rev Cell Dev Biol* 17, 615-675) and this elevation is necessary for anchorage independent growth (Danen, E. H., et al. (2001) *J Cell Physiol* 189, 1-13); Amundadottir, L. T., et al. (1998) *Oncogene* 16, 737-746; Moore, S. M., et al. (1998) *Cancer Res* 58, 5239-5247; Sheng, H., et al. (2001) *J Biol Chem* 276, 14498-14504). Inhibition of this pathway, e.g. by wortmannin or LY294002, induces apoptosis under anchorage-independent conditions (FIGS. 3,4). Thus whether hyaluronan oligomers suppress this pathway was tested.

Figure 5A:
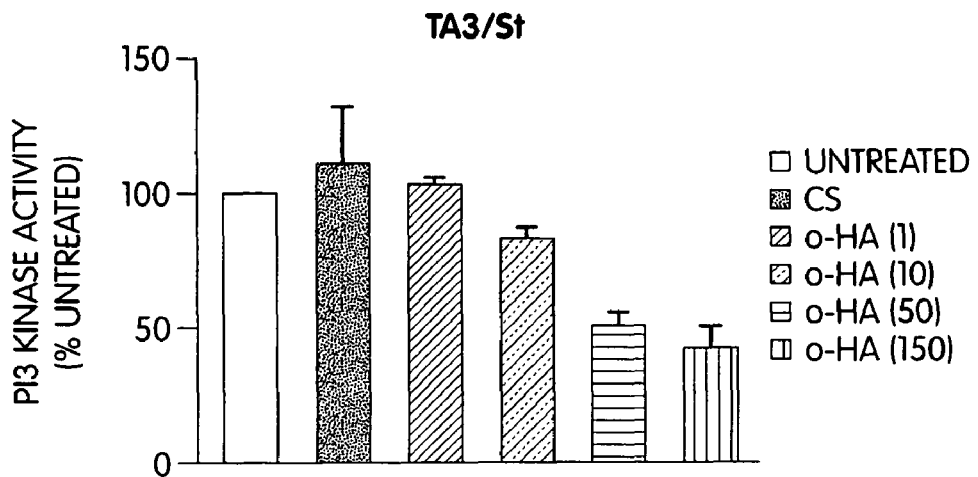
FIG. 5A is a bar graph showing inhibition of PI3 kinase activity in TA3/St murine mammary carcinoma cells by hyaluronan oligomers. Cells were treated in suspension for 24 hours with 1-150 µg/ml hyaluronan oligomers (o-HA) or 150 µg/ml chondroitin sulfate (CS) and analyzed for total PI3 kinase activity. PI3 kinase activity was measured as $^{32}P$-phosphate incorporation into PIP3. Results are calculated as mean±S.D. for three independent experiments and are expressed as a percentage of the value for untreated cells (mean of three experiments±S.D).
Figure 5B:
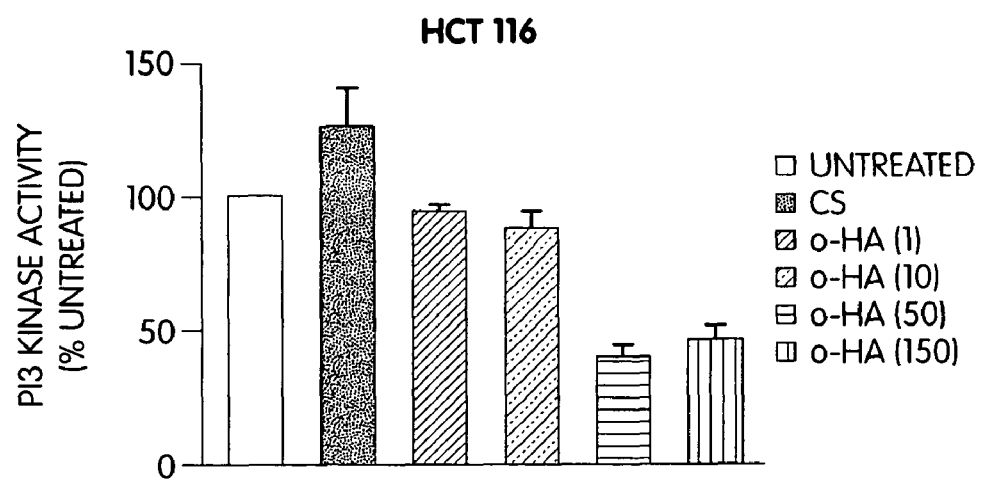
FIG. 5B shows shows measurements similar to those in FIG. 5A with HCT116 human colon carcinoma cells.
Figure 5C:
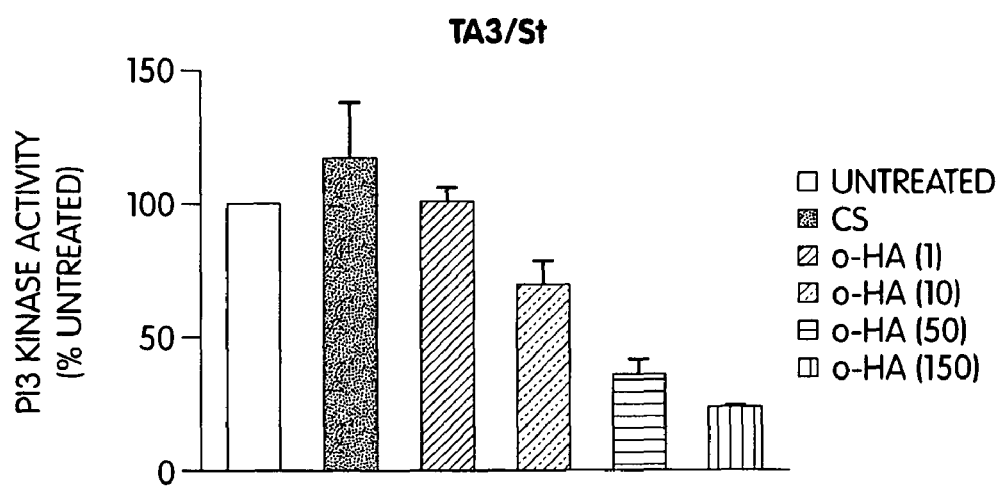
FIG. 5C shows measurements similar to those in FIG. 5A in TA3/St cells except that the α-isoform of PI3 kinase was immunoprecipitated with specific antibody prior to measurement of kinase activity.

The effect of hyaluronan oligomers on total PI3 kinase activity in TA3/St and HCT116 cell extracts was first measured. It was found that addition of 50-150 μg/ml hyaluronan oligomers inhibits total PI3 kinase activity in extracts of these cells by ~60% and that 10 μg/ml sometimes gave partial inhibition (FIGS. 5A, 5B). The effect on the activity of individual PI3 kinase isoforms then was measured. It was found that the predominant isoform present in TA3/St and HCT116 cells was the α isoform. Again, 50-75% inhibition was observed with 50-150 μg/ml hyaluronan oligomers and intermediate effects with 10 μg/ml in both TA3/St cells (FIG. 5C) and HCT116 cells.

Figure 5D:
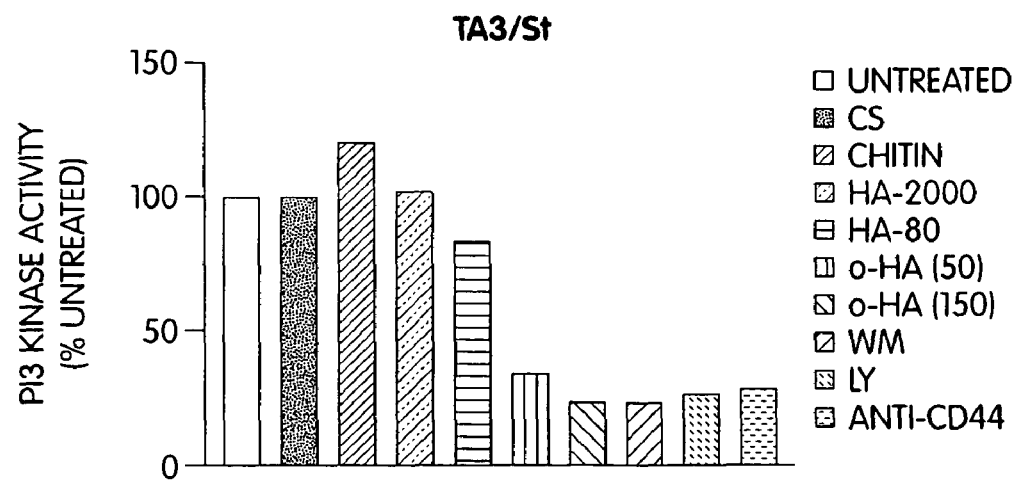
FIG. 5D shows measurements similar to those in FIG. 5C in TA3/St cells, except that cells were treated with 50 and 150 μg/ml hyaluronan oligomers (o-HA), 150 μg/ml chitin oligomers, 150 μg/ml chondroitin sulfate (CS), 150 μg/ml hyaluronan polymer of molecular weights ~80 kDa (HA-80) or ~2,000 kDa (HA-2000), 50 nM wortmannin (WM), 20 μM LY294002 (LY), and 1:50 dilution of antibody to CD44. Similar results to those in FIGS. 5C and 5D were obtained also with HCT116 cells.

Wortmannin and LY294002 had virtually the same effect as that of the oligomers (TA3 1st: FIG. 5D. Similar resuts were obtained with HCT. In addition, the effect of various reagents related to the hyaluronan oligomers was measured. Neither hyaluronan polymer, nor chondroitin sulfate, nor chitin oligomers had a significant effect on PI3 kinase-α activity in TA3/St cells (FIG. 5D) or HCT116 cells. Since different signaling activities have been reported for different sizes of hyaluronan polymer (Turley, E. A., et al. (2002) *J Biol Chem* 277, 4589-4592; Noble, P. W. (2002) *Matrix Biol* 21, 25-29), small (~80 kDa) and large (~2,000 kDa) polymer were tested, and that neither preparation was found to have a significant effect in either cell type.

Figure 6A:
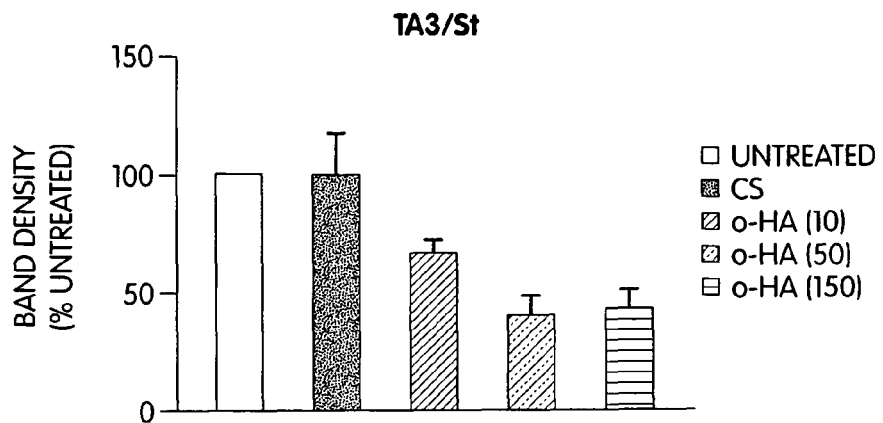
FIG. 6A is a bar graph showing inhibition of Akt phosphorylation by hyaluronan oligomers in TA3/St murine mammary carcinoma cells treated in suspension with 1-150 μg/ml hyaluronan oligomers (o-HA) or 150 μg/ml chondroitin sulfate (CS). Cell lysates were then analyzed by Western blotting for phosphorylated Akt and quantified by densitometry. Results in A and B are presented as means of three independent experiments and expressed as percent untreated±S.D.
Figure 6B:
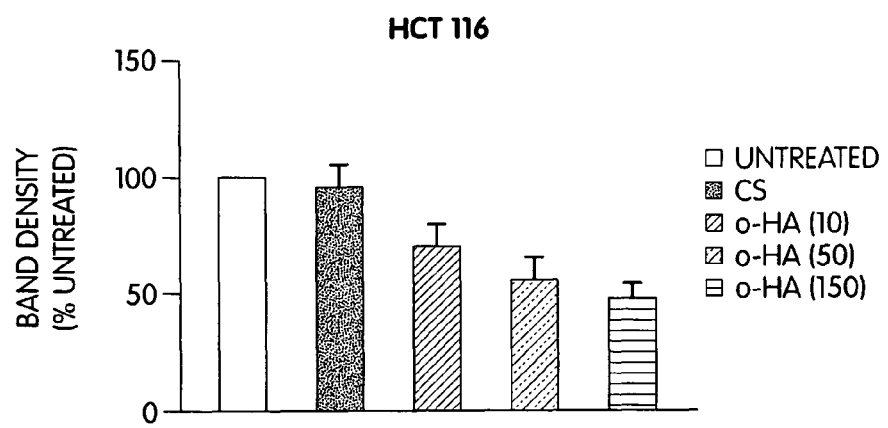
FIG. 6B shows measurements similar to those in FIG. 6A using HCT116 human colon carcinoma cells.
Figure 6C:
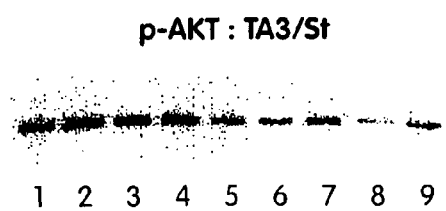
FIG. 6C is a representation of a Western blot of phosphorylated Akt from TA3/St cells: 1. untreated; 2. 150 μg/ml chondroitin sulfate; 3. 150 μg/ml hyaluronan polymer (mol.wt. ~80 kDa); 4. 150 μg/ml chitin oligomers; 5. 50 μg/ml hyaluronan oligomers; 6. 150 μg/ml hyaluronan oligomers; 7. 50 nM wortmannin; 8. 20 μM LY294002; 9. 1:50 dilution of antibody against CD44. Results are representative of three experiments. Similar results to those in FIG. 6C were obtained also with HCT116 cells.

A major target for the PI3 kinase product, PIP3, is 3-phosphoinositide-dependent protein kinase 1 (PDK1) which in turn causes phosphorylation of Akt/protein kinase B (Cantley, L. C., et al. (1999) *Proc Natl Acad Sci USA* 96, 4240-4245). Addition of hyaluronan oligomers caused 50-60% decrease in phosphorylation of Akt in both TA3/St and HCT116 cells (FIG. 6A, 6B). This effect is not caused by chondroitin sulfate, hyaluronan polymer or chitin oligomers and the inhibition by hyaluronan oligomers is similar in magnitude to that of PI3 kinase inhibitors (TA3/St cells: FIG. 6C; similar results were obtained with HCT116 cells). The effects of these reagents on levels of total Akt were also measured but no significant effects were observed in either cell type.

Figure 7A:
FIG. 7A is an immunoblot showing inhibition of phosphorylation of BAD, a protein involved in apoptosis, by HA oligomers in TA3/St murine mammary carcinoma cells. Cells were treated in suspension and then processed for immunoblotting of BAD. Results are representative of two experiments. Phosphorylated BAD shown in cells in lanes: 1. untreated; 2. 150 μg/ml chondroitin sulfate; 3. 150 μg/ml chitin oligomers; 4. 150 μg/ml hyaluronan polymer (mol. wt. ~80 kDa); 5. 50 μg/ml hyaluronan oligomers; 6. 150 μg/ml hyaluronan oligomers; 7. 50 nM wortmannin; 8. 20 μM LY294002; 9. 1:50 dilution of antibody against CD44.
Figure 7B:
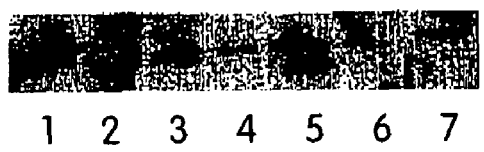
FIG. 7B shows measurements similar to those in FIG. 7A for phosphorylation of FKHR, a nuclear transcription factor, in TA3/St cells treated in lanes: 1. untreated. 2. 150 μg/ml chondroitin sulfate; 3. 150 μg/ml hyaluronan polymer (mol. wt. ~80 kDa); 4. 150 μg/ml hyaluronan oligomers; 5. 50 nM wortmannin; 6. 20 μM LY294002; 7. 1:50 dilution of antibody against CD44. Similar results were obtained for each of phosphorylated BAD and FKHR using HCT116 cells.

Important regulators of apoptosis are BAD and FKHR, both of which are inactivated as a consequence of phosphorylation by Akt (Katso, R., et al. (2001) *Annu Rev Cell Dev Biol* 17, 615-675; Datta, S. R., et al. (1997) *Cell* 91, 231-241; Nakamura, N., et al. (2000) *Mol Cell Biol* 20, 8969-8982). Thus whether treatment with hyaluronan oligomers leads to decreased phosphorylation of these two components was tested. The data show that phosphorylation of BAD and FKHR was inhibited by hyaluronan oligomers (~60%) to a similar extent to that caused by wortmannin or LY294002 (FIGS. 7A, 7B).

Without being limited by any particular theory or mechanism, hyaluronan oligomers may act to displace endogenous hyaluronan from its receptor, CD44, and thus attenuate signaling. If this were the case, blocking antibody to CD44 would be expected to mimic the effect of hyaluronan oligomers. Thus the effects of antibody to CD44 were tested and inhibition of PI3 kinase activity (FIG. 5D), Akt phosphorylation (FIG. 6C), BAD phosphorylation (FIG. 7A) and FKHR phosphorylation (FIG. 7B) was observed to a similar extent to that found with hyaluronan oligomers.

Example 4

Hyaluronan Oligomers Stimulate PTEN Levels

Figure 8A:
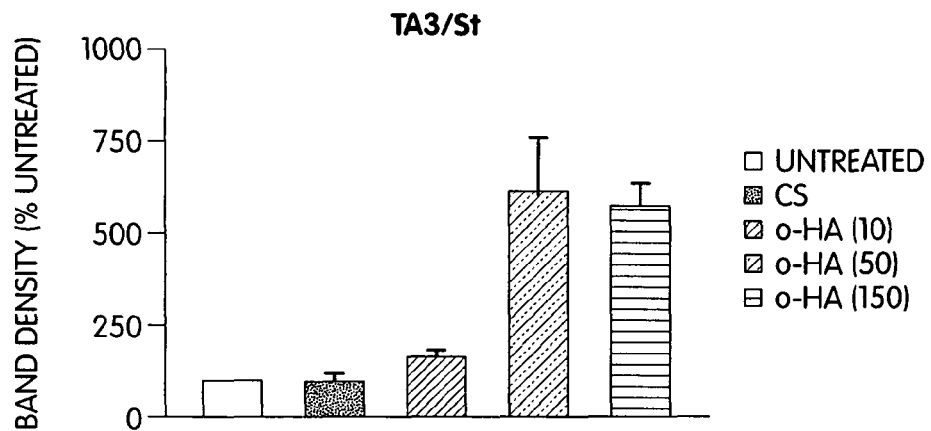
FIG. 8A is a bar graph showing stimulation of expression of PTEN, a tumor suppressor, by HA-oligomers, in TA3/St murine mammary carcinoma cells. Cells were treated in suspension and then processed for immunoblotting of PTEN. The bars represent densitometric quantification of immunoblots after treatment with 10-150 μg/ml hyaluronan oligomers (o-HA) or 150 μg/ml chondroitin sulfate (CS). Results are presented as means of three independent experiments and expressed as percent untreated±S.D.
Figure 8B:
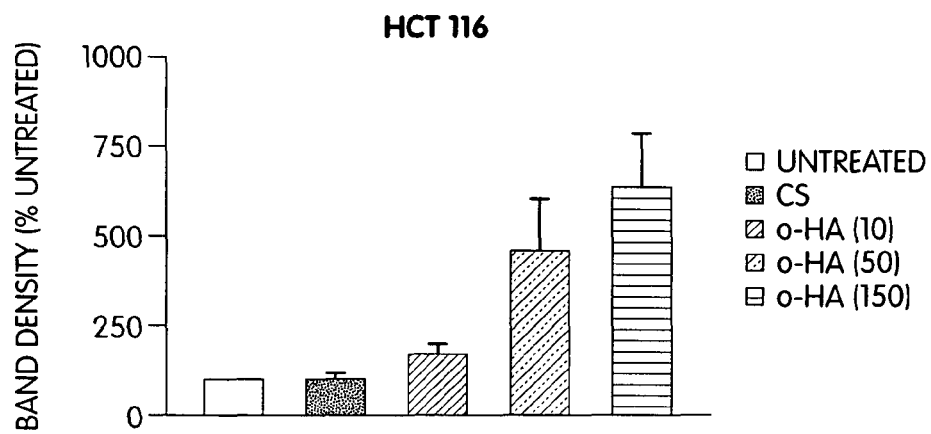
FIG. 8B shows measurements similar to those in FIG. 8A using HCT116 human colon carcinoma cells.
Figure 8C:
FIG. 8C is an immunoblot using TA3/St murine mammary carcinoma cells treated as in lanes: 1. untreated; 2. 150 μg/ml chondroitin sulfate; 3. 150 μg/ml chitin oligomers; 4. 150 μg/ml hyaluronan polymer (mol. wt. ~80 kDa); 5. 50 μg/ml hyaluronan oligomers; 6. 150 μg/ml hyaluronan oligomers. Results are representative of three experiments. Similar results to FIG. 8C were obtained also with HCT116 cells.

An important regulator of the PI3 kinase/Akt pathway is the tumor suppressor, PTEN, a phosphatase that dephosphorylates the PI3 kinase product, PIP3 (Cantley, L. C., et al. (1999) *Proc Natl Acad Sci USA* 96, 4240-4245; Stambolic, V., et al. (1998) *Cell* 95, 29-39). It is observed herein that 50-150 μg/ml hyaluronan oligomers stimulate PTEN by greater than 5-fold in TA3/St and HCT116 cells (FIGS. 8A and 8B, respectively). Similar amounts of hyaluronan polymer, chondroitin sulfate, or chitin oligomers do not stimulate PTEN levels (TA3/St cells: FIG. 8C; similar data were obtained also for HCT116 cells).

Example 5

Retardation of Tumor Growth In Vivo by HA Oligomers

Oligomers containing 6-18 sugar residues are effectively monovalent in their interaction with CD44 (Lesley, J., et al. *J Biol Chem*, 275: 26967-26975, 2000). Thus displacement of endogenous polymeric hyaluronan with oligomers of this size could potentially lead to the loss of hyaluronan-induced signaling.

Figure 9:
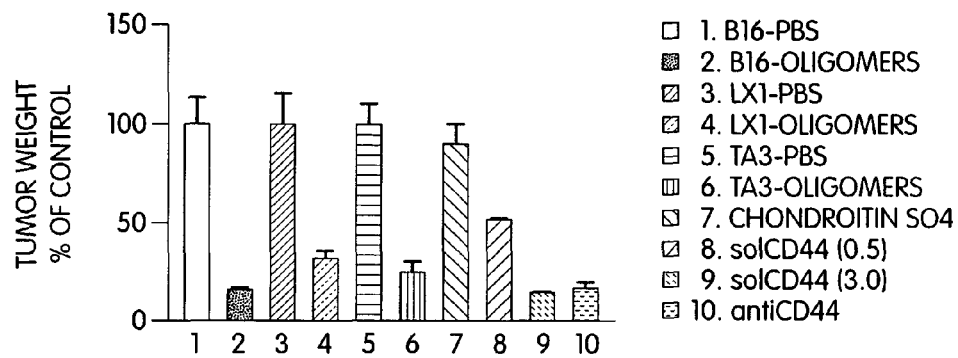
FIG. 9 is a bar graph showing retardation of tumor growth in vivo by HA oligomers. B16 murine melanoma, LX-1 human lung carcinoma, and TA3/St murine mammary carcinoma cells were implanted subcutaneously. Tumors were weighed after 7 days treatment with ALZET pumps containing PBS, 1 mg/ml HA oligomers (0.5 μg/0.5 μl/hr), 0.5 μg/hr chondroitin sulfate (CS), 0.5 or 3.0 μg/hr soluble CD44, or 0.5 μg/hr KM81 CD44 antibody. Each point represents an average of data taken from at least 6 animals±S.E. (See also Ghatak, S., et al. J Biol Chem, 277:38013-20, 2002, the entire contents of which are hereby incorporated by reference herein.)

The HA oligomer preparation was found herein to retard growth of several tumor types in vivo, in a nude mouse system. The tumor types include murine melanoma, murine mammary carcinoma, and human lung carcinoma (see Example 1 herein, and FIG. 9, for data for the tumor types indicated B16, TA3, and LX1, respectively). The weight of melanoma tumors from the HA oligomer treated mice was about 20% that of control mice treated with saline, and was between 30% and 40% of that for the other tumor types. Further, treatment with antibodies that block hyaluronan binding to CD44 inhibited tumor growth and invasion (FIG. 9; Guo, Y., et. Cancer Res, 54: 1561-1565, 1994; Zahalka, M. A., et al. J Immunol, 154: 5345-5355, 1995).

Example 6

Inhibition of Anchorage-Independent Growth in Soft Agar by HA Oligomers or Soluble CD44

Figure 10:
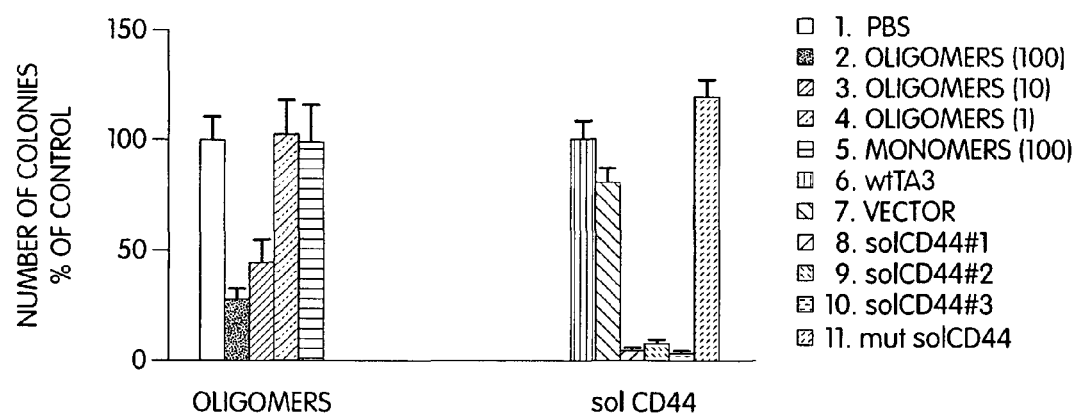
FIG. 10 is a bar graph that shows inhibition of anchorage-independent growth in soft agar by HA oligomers or by over-expression of soluble CD44. Bars 1-5: Growth of TA3/St mouse mammary carcinoma cells in soft agar was inhibited by 10-100 μg/ml HA oligomers. A mixture of 100 μg/ml glucuronate and N-acetylglucosamine, which compose the disaccharide subunit of HA, was used as a negative control. Colonies were counted after 1-2 weeks. Results are means of 3 experiments±S.D. Bars 6-11: Wild type TA3/St, vector transfectant, and mutated soluble CD44 (that does not bind HA) transfectant cells form numerous colonies, but the 3 separate soluble CD44 transfectant clones do not (Peterson, R. M., et al. Am J Pathol, 156: 2159-2167, 2000). Neither HA oligomers nor soluble CD44 significantly affect proliferation in anchorage-dependent, monolayer culture.

Anchorage-independent growth, e.g. in soft agar, is a hallmark characteristic of transformed cells (Freedman, V. H., et al. Cell, 3: 355-359, 1974). Example 2 and FIG. 10 show that perturbation of endogenous hyaluronan interactions, by addition of hyaluronan oligomers, inhibits anchorage-independent growth of several tumor cell types, including breast carcinoma, colon carcinoma and glioma cells (see FIG. 10). The effective concentration of HA oligmers was 10-100 μg/ml. A mixture of the two monosaccharides that comprise the disaccharide subunit of HA, glucuronate and N-acetyl-glucosamine, was ineffective. Further, while soluble CD44 was an effective inhibitor of anchorage-independent growth, the soluble form of a mutated CD44, previously shown not to bind to HA, was ineffective at inhibiting growth.

Example 7

Stimulation of Phosphatase and Tensin (PTEN) Expression by HA Oligomers

Figure 11A:
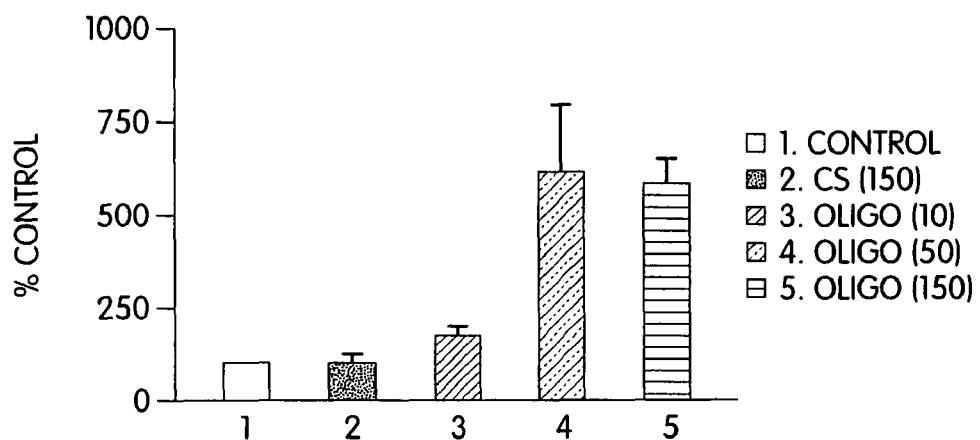
FIG. 11A is a bar graph that shows stimulation of PTEN (phosphatase and tensin) expression by HA oligomers. PTEN levels in TA3/St mouse mammary carcinoma cells were measured by Western blotting; values were obtained by scanning the blots. HA oligomers (oligo) at 50-100 μg/ml caused ~6-fold increase in PTEN levels compared to untreated control. Chondroitin sulfate (CS), polymeric HA and chitin oligomers did not increase PTEN levels.
Figure 11B:
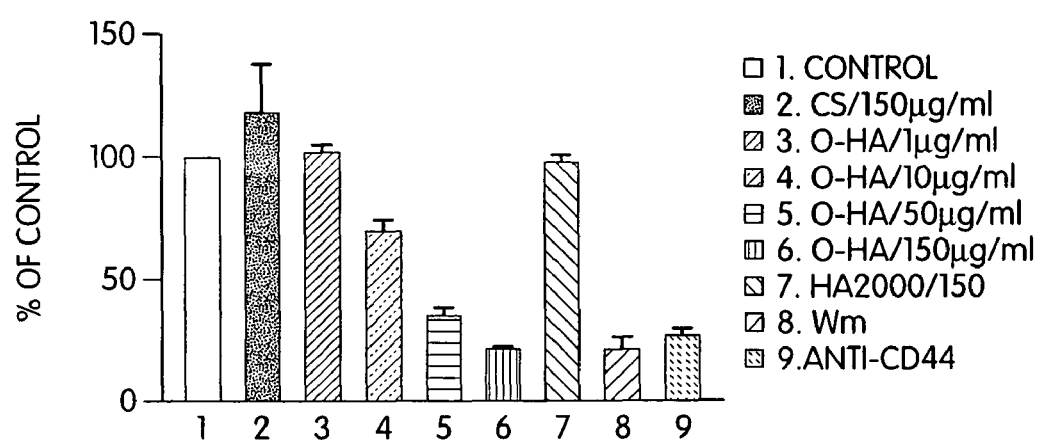
FIG. 11B is a bar graph showing inhibition of PI3 kinase activity by HA oligomers. TA3/St cells were treated with and without HA oligomers (o-HA; 1-150 μg/ml), and CELLS analyzed were for PI3 kinase α activity (assayed by immunoprecipitation of PI3 kinase α, followed by assay of $^{32}$P-phosphate incorporation into PIP3 (Misra, S., et al. Proc Natl Acad Sci USA, 96: 5814-5819, 1999; Susa, M. et al. J. Biol Chem, 267: 38013-20, 2002). 150 μg/ml chondroitin sulfate (CS) or HA polymer (mol wt: 2,000 kDa) had no effect. Treatment with wortmannin (50 nM; Wm) and antibody to CD44 mimicked the effect of HA oligomers. Total PI3 kinase activity was similarly affected.

It is shown herein that treatment of cells with hyaluronan oligomers inhibits anchorage independent growth by a known pathway of intracellular events associated with apoptosis. Effects on this pathway include elevation of PTEN levels (see FIG. 11A), inhibition of phosphoinositol-3-kinase activity (PI3; FIG. 11B), and suppression of numerous downstream events of this cell survival pathway, including phosphorylation of BAD (Bcl-2 associated death) and FKHR (forkhead transcriptional factor) and stimulation of caspase 3 activity and Fas expression.

Figure 13A:
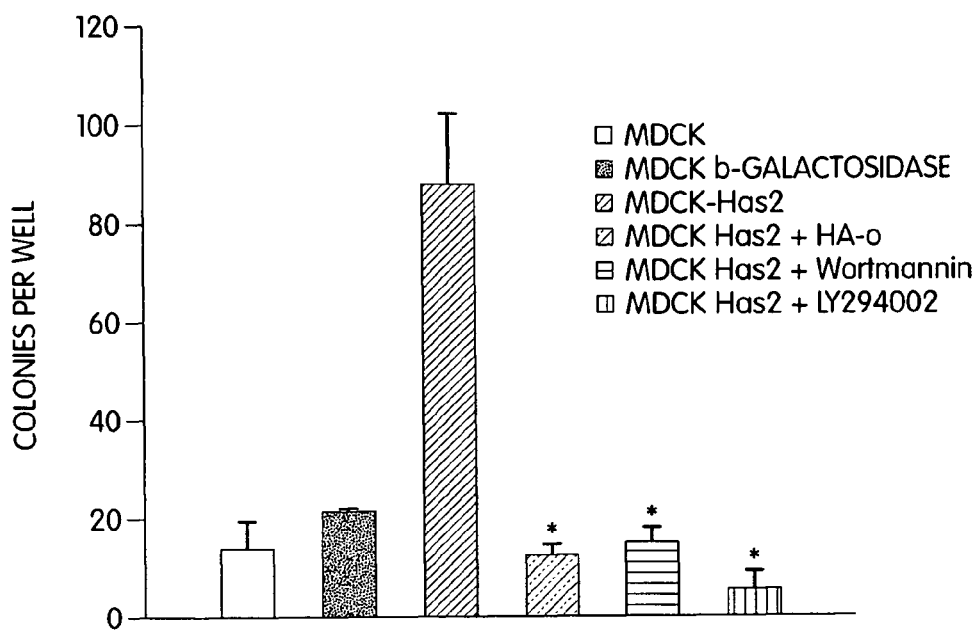
FIG. 13A is a bar graph showing inhibition of colony formation in 0.2% soft agar by MDCK cells infected with an adenovirus vector promoting Has 2 (encoding HA synthetase) expression, by treatment with HA oligomers (100 μg/ml) and by the PI3-kinase inhibitor LY294002 (50 ng/ml). Has-2 cells in the absence of inhibitors show the greatest ability to form colonies, while treatment with HA oligomers, wortmannin, or LY294002 reduced the colony forming ability to that of untransfected control cells, or cells infected with a control vector encoding β-galactosidase.
Figure 13B:
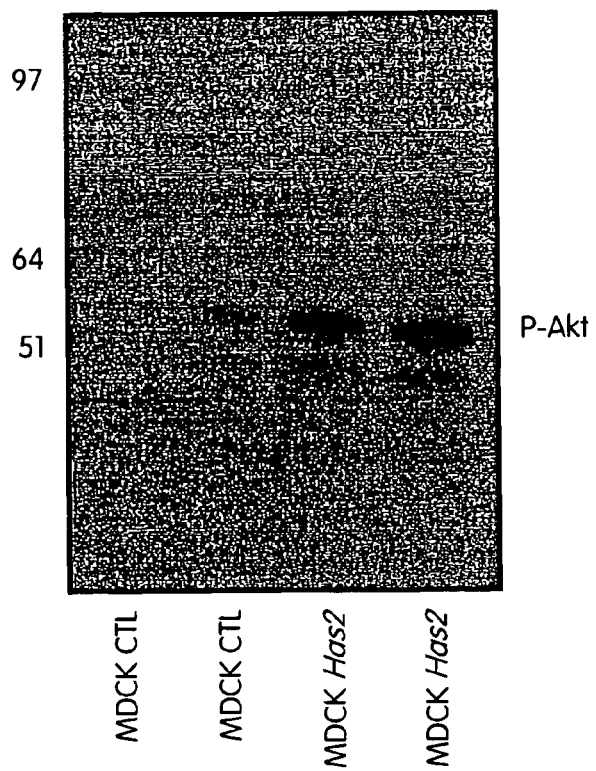
FIG. 13B is a photograph of an SDS-PAGE showing that P-Akt synthesis is elevated in the Has 2 infected cells in comparison to uninfected control cells.

These data are consistent with findings that increased expression of endogenous polymeric HA, induced by various means (for example, treatment with HGF/scatter factor, over-expression of β-catenin, or infection with a Has2 recombinant adenovirus), enhances the cell survival pathway and opposes apoptosis (see example below). Thus MDCK cells infected with the Has2 recombinant adenovirus have enhanced ability to form colones in soft agar (See FIG. 13A) and overepress P-Akt (FIG. 13B), compared to control cells that were not infected. Further, the presence of HA oligomers reversed this effect of infection with a Has2 recombinant adenovirus, as did treatment with wortmannin or HY294002 (FIG. 13A).

Example 8

Resistance of Tumor Cells to Apoptosis-Inducing Drugs

Drug resistance can arise in numerous ways, including decreased uptake of drugs, activation of detoxification mechanisms, and alterations in apoptotic pathways (Gottesman, M. M., et al. Nature Rev Cancer, 2: 48-58, 2002). "Classical" multi-drug resistance (MDR) is usually due to enhanced drug export via the action of ATP-dependent efflux pumps in the mdr, mrp and related ABC transporter families, especially MDR1 (P-glycoprotein), MRP2 (multi-drug resistance-associated protein 2) and BCRP (breast cancer resistance protein). In addition, alterations in apoptotic pathways and multi-drug resistance in cancer cells are interconnected at many levels. Drug resistance in patients may in some cases be overcome by new therapeutic interventions that induce downstream events in the apoptotic cascade (Lowe, S. W. et al. Carcinogenesis, 21: 485-495, 2000; Makin, G. et al. Trends Cell Biol, 11: S22-S26, 2001. O'Gorman, D. M., et al. Leukemia, 15: 21-34, 2001).

Relevant to the embodiments of the invention herein is evidence that many characteristics of multi-drug resistance are dependent on activity of the PI3-kinase/Akt cell survival pathway (O'Gorman, D. M., et al. Leuk Res, 25: 801-811, 2001; Stambolic, V., et al. Cell, 95: 29-39, 1998; Yang, J. M., et al. Biochem Pharmacol, 63: 959-966, 2002; Kuo, M. T., et al. Oncogene, 21: 1945-1954, 2002). Since HA oligomers suppress this pathway, it is possible that HA oligomers would reverse resistance to these agents. Further, hyaluronidase enhances the action of various chemotherapeutic agents, especially when used locally (Baumgartner, G., et al. Cancer Lett, 131: 85-99, 1998). Treatment of multicellular spheroids of EMT-6 mammary tumor cells with hyaluronidase reverses MDR1-based multi-drug resistance (Croix, B. S., et al. J Natl Cancer Inst, 88: 1285-1296, 1996; St Croix, B., et al. Cancer Lett, 131: 35-44, 1998). The mechanistic effect of hyaluronidase is not understood but has usually been explained in terms of the effects of decreased cell adhesion and increased drug penetration, rather than effects on cell survival signaling as found herein.

Effect of addition of hyaluronan oligomers on resistance of MDA-MB231 human breast cancer cells to treatment with methotrexate was assessed. The mechanism of resistance of tumor cells to methotrexate is somewhat controversial; studies have demonstrated methotrexate-specific, decreased uptake by the reduced folate carrier (Worm, J., et al. J Biol Chem, 16: 16, 2001; Ma, D., et al. Biochem Biophys Res Commun, 279: 891-897, 2000) and more "classical" effects such as increased efflux mediated by members of the MRP family or related transporters (Hooijberg, J. H., et al. Cancer Res, 59: 2532-2535, 1999; Kool, M., et al. Proc Natl Acad Sci USA, 96: 6914-6919, 1999; Volk, E. L., et al. Cancer Res, 60: 3514-3521, 2000). It is here found that addition of 100 µg/ml of hyaluronan oligomer caused a surprising sensitization of the MB231 cells to methotrexate, decreasing the $IC_{50}$ from approximately 1 µM to 10 nM, a 100-fold improvement of the effectiveness of methotrexate (FIG. 12, in which the MB231 cells are indicated "MDA"). Further, no oligomer effect was obtained with methotrexate-sensitive MCF-7 cells. These data indicate that use of HA oligomers to overcome cellular multi-drug resistance can render classical chemotherapeutic agents active at much lower concentrations, which is also of value in sparing side effects in the patient.

Example 9

Effect of HA Oligomers on Resistance of Human Cancer Cell Lines to Commonly Used Chemotherapeutic Drugs To extend the showing that HA oligomers sensitize MDA-MB213 cells to methotrexate, a more widely used system for studying multi-drug resistance, i.e. MCF-7/adrR cells is used for studies similar to those herein.

These cells, of human breast carcinoma origin, were selected for resistance to doxorubicin and have been shown to exhibit multi-drug resistance due to up-regulation of MDR1 (Fairchild, C. R., et al Cancer Res, 47: 5141-5148, 1987) and the drug-detoxifying enzyme, glutathione S-transferase (Batist, G., et al. J Biol Chem, 261: 15544-15549, 1986). The MCF-7/adrR cells were obtained from Dr. Kenneth Cowan of the Eppley Cancer Center, Nebraska.

Using these cells, the relative degrees of resistance of MCF-7 and MCF-7/adrR cells to doxorubicin, paclitaxel and vinblastine are assessed, in the presence and absence of HA oligomers. HA oligomers alone, in the absence of chemotherapeutic agents, have little or no effect on proliferation in monolayer culture.

Figure 12:
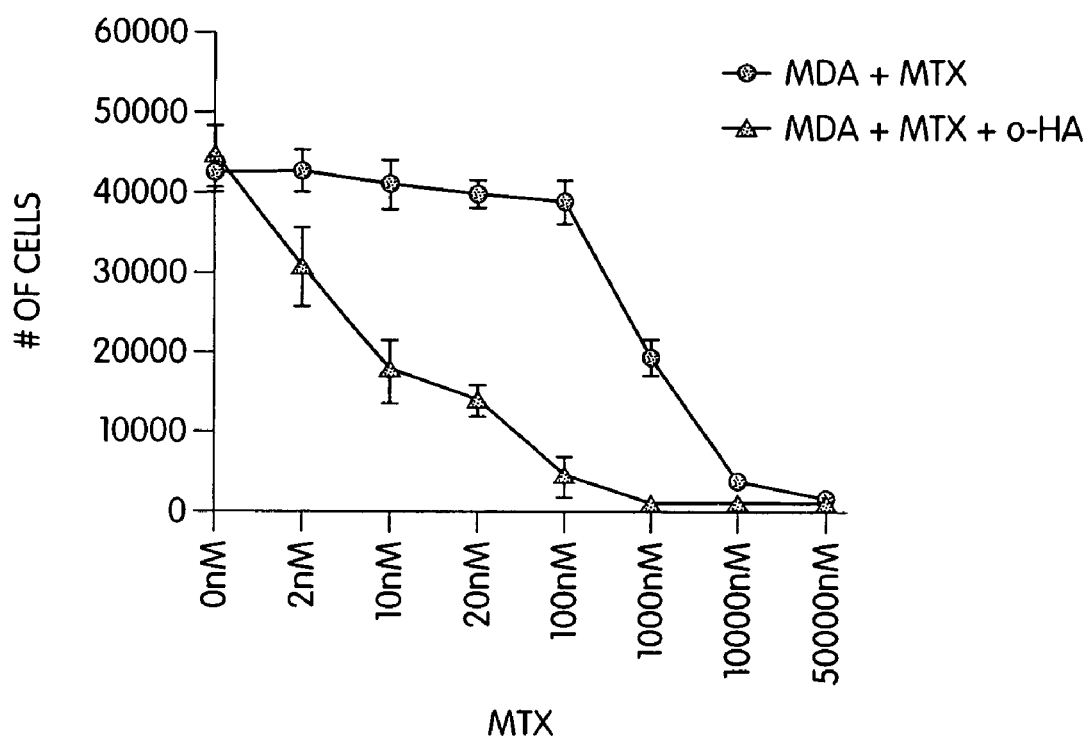
FIG. 12 is a line graph that shows reversal of resistance to methotrexate by HA oligomers. MDA-MB231 human mammary carcinoma cells were treated with increasing concentrations of methotrexate (MTX) in the presence or absence of 100 μg/ml HA oligomers. Cells were grown in monolayer culture in 10% fetal bovine serum and cell number measured in a coulter counter. The MTT assay for viable cells (Denizot, F., et al. J Immunol Methods, 89: 271-277, 1986) gave similar results. Under these anchorage-dependent conditions HA oligomers alone do not significantly affect cell proliferation or apoptosis.

Doxorubicin, paclitaxel and vinblastine represent three classes of drugs, i.e. anthracyclines, microtubule stabilizers and vinca alkaloids, respectively, which are commonly affected by "classical" multi-drug resistance, and MCF-7/adrR cells have been shown to be resistant to these three drugs (Fairchild, C. R., et al Cancer Res, 47: 5141-5148, 1987; Zilfou, J. T, et al. Oncol Res, 7: 435-443, 1995; Ogretmen, B., et al. Int J Cancer, 67: 608-614, 1996; Hall, J. G., et al. Adv Enzyme Regul, 39: 113-128, 1999; and Ciardiello, F., et al. Int J Cancer, 98: 463-469, 2002). These experiments are performed in a similar manner to Examples above with methotrexate (FIG. 12). Cells are grown in DMEM containing 10% fetal bovine serum plus 10-250 µg/ml HA oligomers and a range of concentrations of doxorubicin, paclitaxel or vinblastine. Two sources of highly purified HA oligomers, from Anika Therapeutics Inc and from Seikagaku Inc, are used (Zeng, C., et al. Int J Cancer, 77: 396-401, 1998). Cell numbers are measured by counting cells in a Coulter counter and by the MTT assay for viable cells (Volk, E. L., et al. Cancer Res, 60: 3514-3521, 2000).

To determine whether the HA oligomers affect drug accumulation in the tumor cells, uptake and efflux of doxorubicin in MCF-7/adrR cells and of methotrexate in MDA-MB231 cells are measured. Doxorubicin uptake and efflux will be measured as described (Fu, L. W., et al. Eur J Cancer, 38: 418-426, 2002). Briefly, MCF-7 and MCF-7/adrR cells will be incubated with 10 µM doxorubicin, plus or minus HA oligomers, in medium supplemented with 10 mM glucose for 3 hours, followed by processing of washed cells in 0.3M HCl and 60% ethanol, centrifugation and spectrofluorometric measurement of doxorubicin at 470 nm (excitation) and 590 nm (emission). To measure efflux, the same procedure will be used except that, after the incubation described above, the cells will be washed and further incubated without doxorubicin, with and without HA oligomers. Methotrexate uptake and efflux will be measured in a similar manner, but using a radioactive assay with $^3$H-methotrexate (Amersham; Worm, J., et al. J Biol Chem, 16: 16, 2001).

These Examples are performed under anchorage-dependent conditions. Data herein demonstrate that HA oligomers induced apoptosis and suppressed the PI3-kinase/Akt cell survival pathway under anchorage-independent conditions (FIGS. 3 and 11). However, HA oligomers also suppressed this pathway to a moderate extent under anchorage-dependent conditions. This level of suppression, while not sufficient to induce apoptosis under anchorage-dependent conditions, can be capable of sensitizing cells under these conditions to chemotherapeutic agents. Thus, whether the HA oligomers stimulate PTEN expression and suppress PI3-kinase activity, Akt and BAD phosphorylation is determined in these cells under the conditions of drug treatment used here. These measurements are performed by methods that are standard in the art (Ghatak, S., et al. J Biol Chem, 277:38013-20, 2002).

An appropriate range of concentrations of doxorubicin, paclitaxel and vinblastine for assessing the $IC_{50}$ for inducing apoptosis in MCF-7 and MCF-7/adrR cells is determined. The effect of 10-250 µg/ml hyaluronan oligomers on the $IC_{50}$ for these drugs is tested. Uptake and efflux of doxorubicin in MCF-7/adrR cells is measured under conditions wherein the hyaluronan oligomers maximally reverse resistance. Uptake and efflux of methotrexate in MDA-MB231 cells is measured under conditions wherein the hyaluronan oligomers maximally reverse resistance (as determined in pilot studies). The effect of doxorubicin, paclitaxel and vinblastine is measured, plus/minus hyaluronan oligomers, on parameters such as phosphoinositide-3-kinase activity (PI3-kinase), phosphorylation of Akt (protein kinase 3) and BAD, and expression of PTEN in MCF-7/adrR cells.

Example 10

Effect of HA Oligomers on Chemoresistance of Human Cancer Cells in Spheroid Cultures Numerous studies have demonstrated that drug resistance is often increased under conditions where cell interactions take place in three dimensions, e.g. in spheroids, a phenomenon sometimes called multi-cellular resistance (DeSoize, B. et al. Crit Rev Oncol/Hematol 36:193-207, 2000; Olive, P. L. et al. Cancer Metastasis Rev, 13: 121-138, 1994; and Kerbel, R. S., et al. Cold Spring Harb Symp Quant Biol, 59: 661-672, 1994). Such resistance can sometimes be reversed by treatment with hyaluronidase (Croix, B. S., et al. J Natl Cancer Inst, 88: 1285-1296, 1996; St Croix, B., et al. Cancer Lett, 131: 35-44).

The relative resistance of MCF-7 and MCF-7/adrR cells to doxorubicin, paclitaxel and vinblastine grown in this manner in the presence and absence of varying concentrations of HA oligomers is measured. Previous studies have shown that spheroid culture increases drug resistance in the relatively sensitive MCF-7 cells (dit Faute, M. A., et al. Clin Exp Metastasis, 19: 161-168, 2002). Spheroid cultures will be set up as described (Ballangrud, A. M., et al. Clin Cancer Res, 5: 3171s-3176s, 1999), i.e. by growing the cells on the top of a thin agar layer, followed by selection of about 1-200 µm spheroids and transfer to agar layers in 24-well plates. The effects of drug/oligomer combinations will be measured by assessing spheroid volume (Ballangrud, A. M., et al. Clin Cancer Res, 5: 3171 s-3176s, 1999) or by the MTT viability assay (Denizot, F. et al. J Immunol Methods 89: 271-277, 1986).

Spheroid cultures of MCF-7 and MCF-7/adrR cells will be established. An appropriate range of concentrations of doxorubicin, paclitaxel and vinblastine for assessing the $IC_{50}$ for inducing apoptosis in spheroid cultures will be determined. Then the effects of 10-250 µg/ml hyaluronan oligomers on the $IC_{50}$ for the above drugs is tested.

Example 11

Effect of HA Oligomers on Chemoresistance in Nude Mice Xenografts of Human Cancer Cells Effects on chemoresistance in culture systems do not always reflect relative efficacy in vivo. Thus the effect of HA oligomers on resistance to doxorubicin will be measured in vivo, using xenografts of MCF-7/adrR cells into experimental animals.

Xenografts will be set up as described previously (Fu, L. W., et al. Eur J Cancer, 38: 418-426, 2002; Ullman, C. Anticancer Res. 11: 1379-1382, 1991). Briefly, $0.5 \times 10^6$ cells will be injected s.c. into nude mice. After reaching a size of about 5×5 mm, the mice will be divided into groups of 6, and each is injected i.p. with either doxorubicin alone (4 mg/kg), HA oligomers alone (5 mg/kg) or doxorubicin (4 mg/kg) plus HA oligomers (5 mg/kg) every second day for 3-4 weeks. Further, the doxorubicin will be administered i.p. and the HA oligomers (0.5 µg/0.5 µl HA/hour) or PBS will be administered from 3-week ALZET pumps implanted next to the injection site as in above experiments. Tumor volume is estimated from measurements of diameter at regular intervals. Tumor weights are measured upon sacrifice after 4 weeks.

Xenografts of MCF-7/adrR cells will be set up subcutaneously (s.c.) in nude mice, and appropriate doses of doxorubicin for $IC_{50}$ determination will be assessed. The effect on tumor growth of intraperitoneal (i.p.) administration compared to s.c. administration from ALZET pumps of hyaluronan oligomers alone is assessed. The effect of hyaluronan oligomers on $IC_{50}$ for doxorubicin is tested at doses of oligomers that have little or no effect alone, and at doses that have significant effects alone.

Recent investigations have demonstrated the importance of normal cell-extracellular matrix interactions in suppressing malignant behavior and the potential role of aberrant cell-matrix interactions in the onset and progression of malignant characteristics (e.g. see (Bissell, M. J., et al. Cancer Res, 59: 1757-1763s; and 1763s-1764s, 1999; Roskelley, C. D. et al. Semin Cancer Biol, 12: 97-104, 2002). HA is one of the matrix components that have been implicated in tumor progression. It is shown herein that increased HA expression enhanced the activity of the PI3-kinase/Akt cell survival pathway, and that small oligomers of HA antagonized the effect of endogenous HA polymer interactions by suppressing the PI3-kinase/Akt cell survival pathway and inducing apoptosis under anchorage-independent conditions. Without being limited by any particular mechanism, it is proposed that HA oligomers may sensitize chemoresistant cancer cells by suppressing the cell survival pathway and sensitizing cells to apoptotic mechanisms. Examples herein show that HA oligomers retard tumor growth in vivo. The possibility that these oligomers also reverse chemoresistance, may lead to novel treatments that enhance current chemotherapeutic protocols by more effective killing of cancer cells with few side effects.

Example 12

Effect of HA Oligmers on Radiation Resistance of Tumor Cells

Treatment of cells with hepatocyte growth factor (HGF; also known as scatter factor) or increased expression of β-catenin induces transformed properties in epithelial cells. In the case of β-catenin, these transformed properties include increased resistance to γ-irradiation, and increased transition through S1 phase, compared to controls (Orford, K. et al. 1999 J Cell Biol 146: 855-868).

Figure 14A:
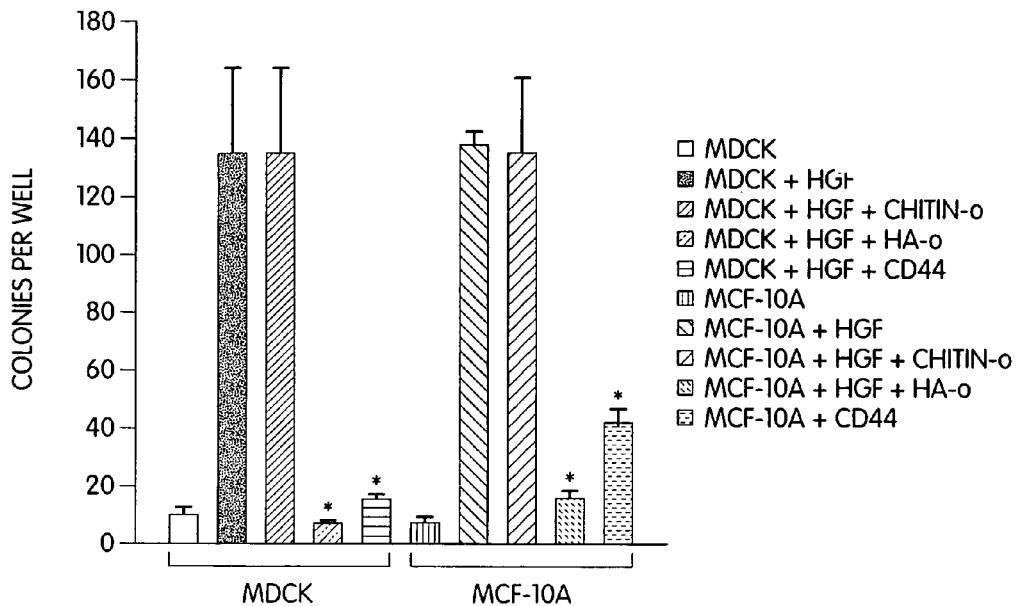
FIG. 14A is a bar graph showing that treatment of HGF-stimulated MDCK or MDCK-10A cells with HA oligomers (100 μg/ml) causes reversal of ability of cells to form colonies in 0.2% soft agar. Antibody to CD44 (10 μg/ml) had a similar inhibitory effect, however chitin oligomer treatment (100 μg/ml) did not reverse ability to form colonies. Colonies less than 150 μm were excluded from the analysis; * indicates a p<0.05, compared to untreated cells.
Figure 14B:
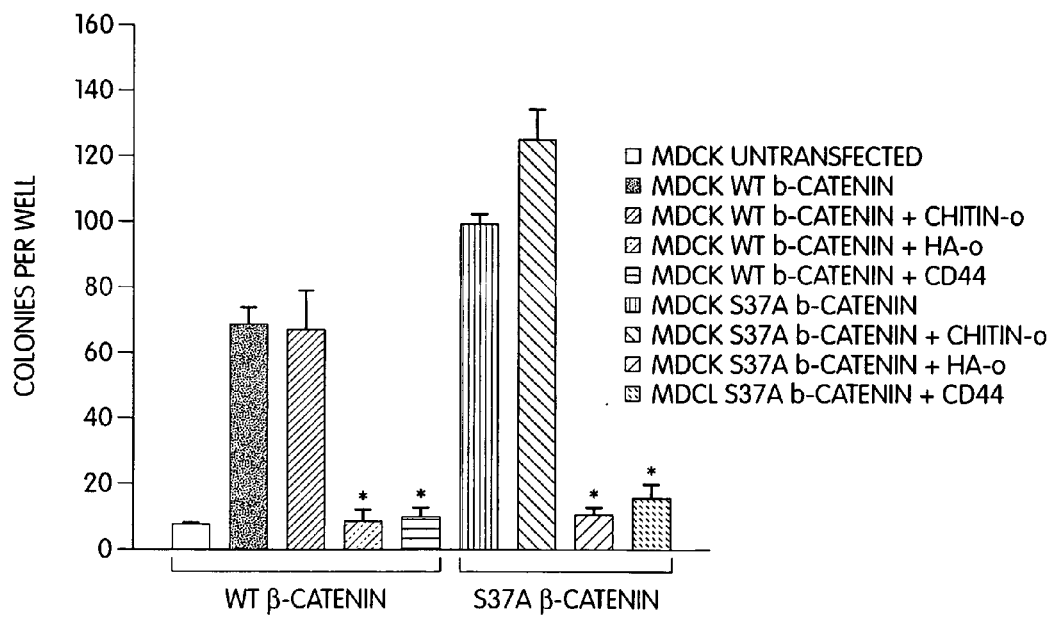
FIG. 14B is a bar graph showing that β-catenin over-expressing MDCK or MDCK-37A cells with HA oligomers caused reversal of colony forming ability in 0.2% soft agar. Antibody to CD44 had a similar inhibitory effect, however chitin oligomer treatment does not reverse ability to form colonies. Other conditions were as described for FIG. 14A.
Figure 14C:
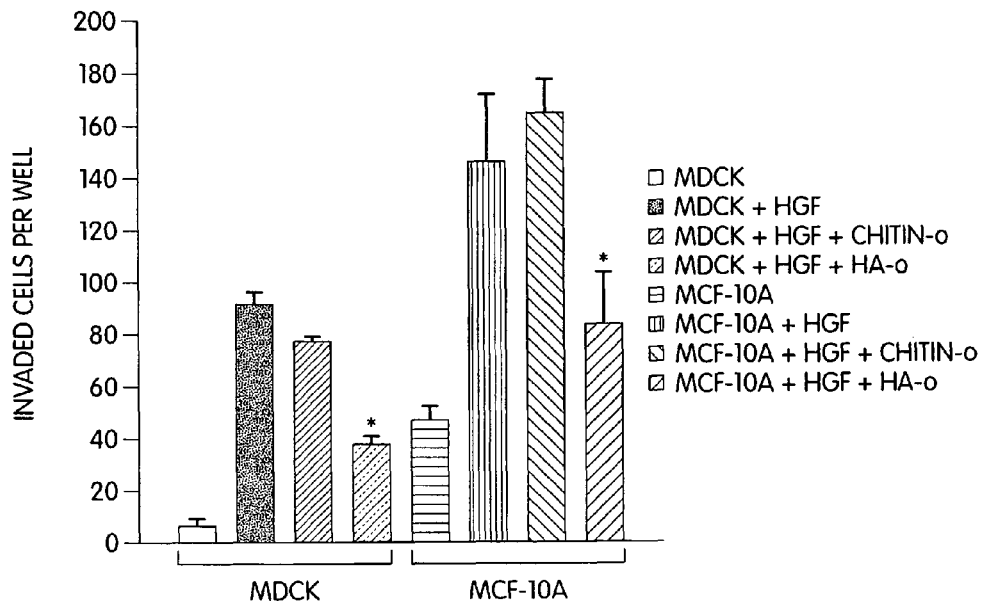
FIG. 14C is a bar graph showing that treatment of the HGF-stimulated MDCK or MDCK-10A cells as described in FIG. 15A with HA oligomers caused reversal of ability of cells to invade through Matrigel coated chambers.
Figure 14D:
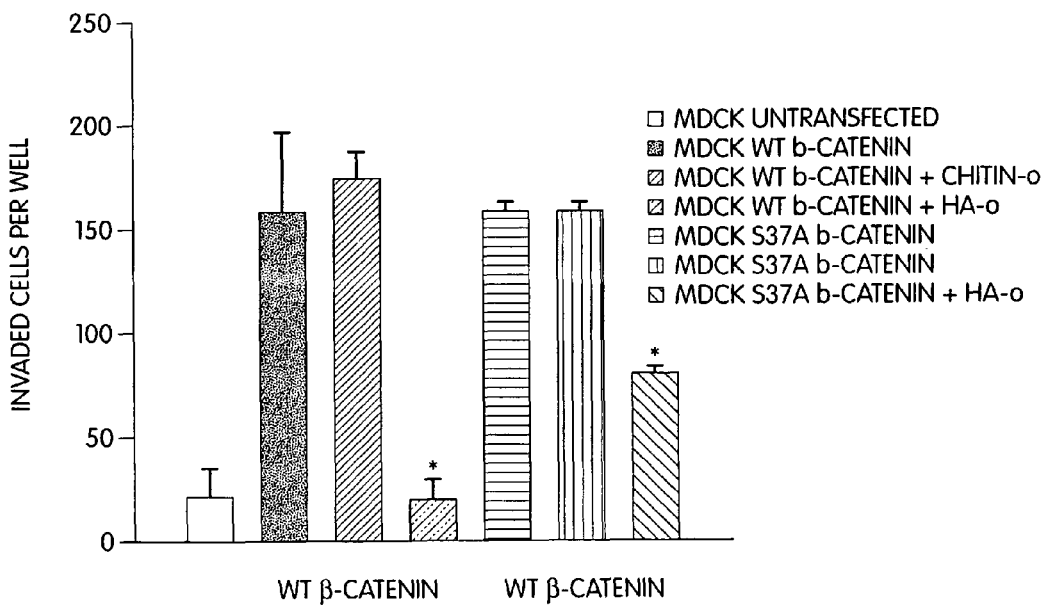
FIG. 14D is a bar graph showing that treatment of the β-catenin over-expressing MDCK or MDCK-37A cells with HA oligomers caused reversal of ability to invade through Matrigel coated chambers.

As shown herein, HGF treatment or increased β-catenin expression induced anchorage-independent growth in MDCK cells, was reversed by treatment with HA oligomers, and also with anti-CD44 antibodies (FIGS. 14A,14B). Further, these cells were found to be capable of invading a Matrigel coated chamber, and HA oligomers but not chitin oligomers was able to reverse this invasiveness. Thus treatment with HA oligomers to improve susceptibility of cells to irradiation is further examined.

For this purpose, MDCK cell lines were constructed which are vector-transfected and β-catenin-transfected. These cells will be exposed to 5 Gy (Gray units) of γ-irradiation for 8-24 hours, and their cell cycle characteristics analyzed by FACS, in comparison to control cells that have not been irradiated. Further, this experiment will be performed in the presence and absence of 10-500 μg/ml HA oligomers, to determine whether or not the oligomers reverse this effect and cause growth arrest. Similar controls to those used above will be included.

Example 13

Effect of HABP on Susceptibility of Cells to Multi-drug Resistance and Radiation Resistance The effect of over-expression of soluble HABPs on each of multi-drug resistance and radiation resistance is tested, using recombinant adenovirus vectors capable of promoting synthesis of soluble CD44 and the brevican link module, i.e., hyaluronan-binding domain of brevican, which is a hyaluronan-binding proteoglycan derived from brain.

Without being bound by any particular mechanism, the mutated CD44 described herein will be further used to confirm that any positive effect of increased susceptibility of cells to drugs or radiation in the presence soluble CD44 is due to the specificity of HA affinity by the HABP These data will determine whether competition for endogenous HA mimics the effect of HA oligomers. Levels of PI3 kinase activity, Akt phosphorylation and PTEN expression in each of HA oligomer- and soluble HABP-treated vs untreated cells used in these experiments can be determined, to confirm the effect of these compositions on the apoptotic pathway.

Example 14

Hyaluronan Oligomers Increase Sensitivity of an Adriamycin-Resistant Cell Line to Doxorubicin, Methotrexate, BCNU, Taxol and Vincristine It is shown herein that perturbation of hyaluronan-cell interactions induces apoptosis in malignant cancer cells under anchorage-independent and conditions. Under these conditions, normal epithelial cells undergo apoptosis since integrin-mediated attachment to extracellular matrix macromolecules is required for their survival. However, many types of cancer cells have escaped this requirement for survival and can be grown in suspension or in soft agar, in large part due to constitutive enhancement of cell survival pathways such as the phosphoinositide-3 (PI3) kinase/Akt and MAP kinase signaling cascades (Frisch, S. M., et al. Curr Opin Cell Biol 13, 555-62, 2001; Tamura, M. et al., J Natl Cancer Inst 91, 1820-8 (1999); Almeida, E. A. et al., J Cell Biol 149, 741-54, 2000).

Endogenous hyaluronan interactions were perturbed above by treatment with hyaluronan oligosaccharides (~1200-4000 Da); these oligomers compete for endogenous polymeric hyaluronan, thus replacing high affinity, multivalent and cooperative interactions with low affinity, low valency receptor interactions (Underhill, C. B., et al. J Biol Chem 258, 8086-91, 1983; Lesley, J., et al., J Biol Chem 275, 26967-75, 2000). The hyaluronan oligomers suppressed the PI3-kinase/Akt cell survival pathway, leading to pro-apoptotic events such as decreased phosphorylation of BAD and FKHR, increased PTEN expression and increased caspase-3 activity. It is here found that these changes in signaling pathways take place under anchorage-dependent as well as anchorage-independent conditions. Since, as explained above, multi-drug resistance is often dependent on cell survival signaling pathways, it was postulated that hyaluronan oligomers might reverse this resistance.

Therefore, the effect of co-treatment with hyaluronan oligomers on drug resistance was examined in an established system, i.e. MCF-7/Adr human mammary carcinoma cells that have been selected for resistance to doxorubicin (Fairchild, C. R., et al., Cancer Res 47, 5141-8, 1987). First, the effect of hyaluronan oligomers on resistance to doxorubicin in the MCF-7/Adr cells versus the relatively drug-sensitive, parental MCF-7 cell line was compared. It was found that 100 μg/ml hyaluronan oligomers caused ~55-fold sensitization of the MCF-7/Adr cells to the drug, but had little effect on the already sensitive MCF-7 cells (FIGS. 15A, 15B; Table 1). A range of concentrations of the oligomers was tested and it was found that, whereas concentrations up to 200 μg/ml had little or no effect on cell survival when used alone, concentrations of 10 μg/ml or more had a significant effect on doxorubicin resistance.

TABLE 1

Effect of hyaluronan oligomers on $IC_{50}$ values (micromolar).

| cells: | MCF-7/Adr | MCF-7/Adr + o-HA | MCF-7 | MCF-7 + o-HA |
|---|---|---|---|---|
| Doxorubicin | 2.20 | 0.04 | 0.03 | 0.04 |
| BCNU | 14.0 | 0.18 | 0.50 | 1.20 |
| Taxol | 0.70 | 0.06 | 0.35 | 0.35 |
| Vincristine | 0.20 | 0.02 | 0.03 | 0.03 |

| | MDA-MB231 | MDA-MB231 + o-HA | MCF-7 | MCF-7 + o-HA |
|---|---|---|---|---|
| Methotrexate | 0.80 | 0.006 | 0.02 | 0.02 |

Figure 16A:
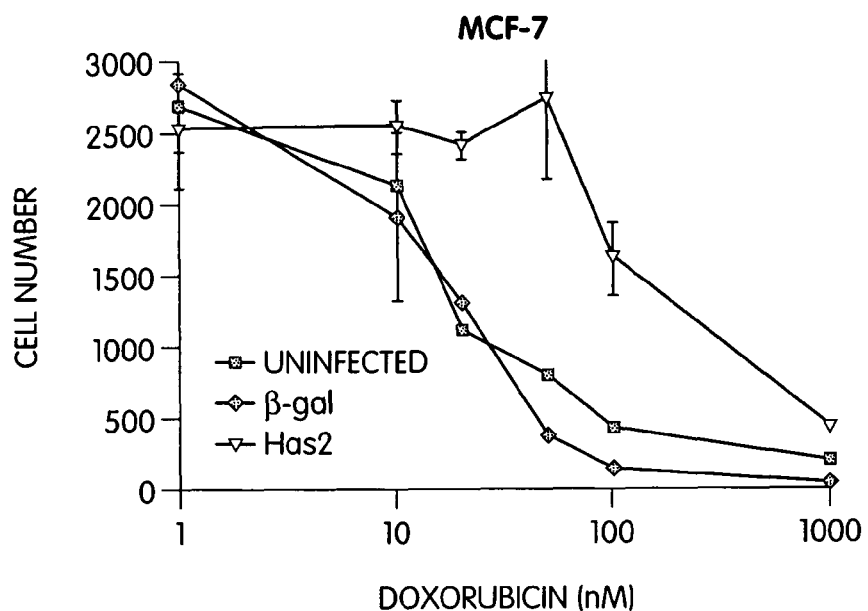
FIG. 16A is a line graph showing increased expression of hyaluronan induced doxorubicin resistance in carcinoma cells. MCF-7 cells were infected overnight with a recombinant Has2 adenovirus or a control β-galactosidase adenovirus (β-gal), constructed and used as described previously (O'Gorman, D. et al. Leuk Res, 25: 801-811, 2001. Stambolic, V., et al. Cell, 95: 29-39, 1998). Untreated MCF-7 cells or cells infected overnight with a recombinant Has2 adenovirus or a control β-galactosidase adenovirus (β-gal) were washed, then treated in culture for 48 h with 1-1000 nM doxorubicin, followed by analysis of cell number. IC50 values: uninfected, 18 nM; β-galactosidase, 20 nM; Has2, 210 nM.

MCF-7/Adr, MCF-7, or MDA-MB231 cells were treated with a range of drug concentrations, with and without 100 μg/ml hyaluronan oligomers (o-HA), as in FIG. 16A.

The effect of hyaluronan oligomers on resistance of these cells to other drugs was tested, i.e. whether they affect multi-drug resistance. The oligomers were found herein to decrease resistance to taxol by ~12-fold, 1,3 bis(2-chloroethyl)-1-nitrosurea (BCNU) by ~78-fold, and vincristine by ~10-fold (Table 1). Again, the oligomers had little effect on the parental MCF-7 cells (Table 1).

The hyaluronan oligomers were also tested in a different cell system, i.e. resistance of MDA-MB231 human mammary carcinoma cells to the folate analog methotrexate (Worm, J., et al., *J Biol Chem* 16, 16, 2001); it was herein found that they decreased resistance in this system by 133-fold (Table 1).

Example 15

Hyaluronan Expression Induces Drug Resistance in Carcinoma Cells, an Effect that is Reversed by Hyaluronan Oligomer Treatment If the hyaluronan oligomers sensitize multi-drug resistant cells by perturbing hyaluronan interactions, then increased hyaluronan production might be expected to cause increased resistance in drug-sensitive cells. Thus hyaluronan production was stimulated in the relatively drug-sensitive MCF-7 cells, by infection with a recombinant adenovirus driving expression of HAS2, one of the enzymes that synthesize hyaluronan (Weigel, P. H., et al. *J Biol Chem* 272, 13997-4000, 1997).

Figure 16B:
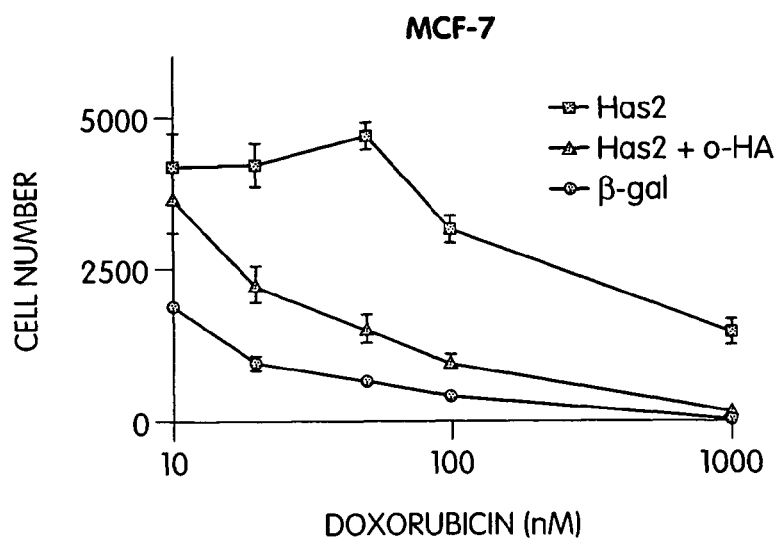
FIG. 16B is a line graph showing reversal of hyaluronan induced doxorubicin resistance in o-HA treated recombinant Has2-adenovirus-infected MCF-7 cells. Cells were treated in culture for 48 h with 10-1000 nM doxorubicin in the presence or absence of 100 μg/ml o-HA and analyzed as in FIG. 16A.

In three separate experiments, the HAS2 adenovirus-infected cells were found to produce 2.5-4 times more hyaluronan than untreated cells or control cells infected with recombinant β-galactosidase adenovirus (FIG. 16A). Further, increased hyaluronan production induced a 10-12-fold increase in resistance to doxorubicin (FIG. 16B), which resistance is reversed by continuous treatment with hyaluronan oligomers (FIG. 16C).

Preliminary data showed that emmprin, a a glycoprotein and a member of the Ig superfamily that is enriched on the surface of most malignant cancer cells (Biswas, C., et al. *Cancer Res* 55:434-439, 1995), regulates hyaluronan production in tumor cells.

Figure 16C:
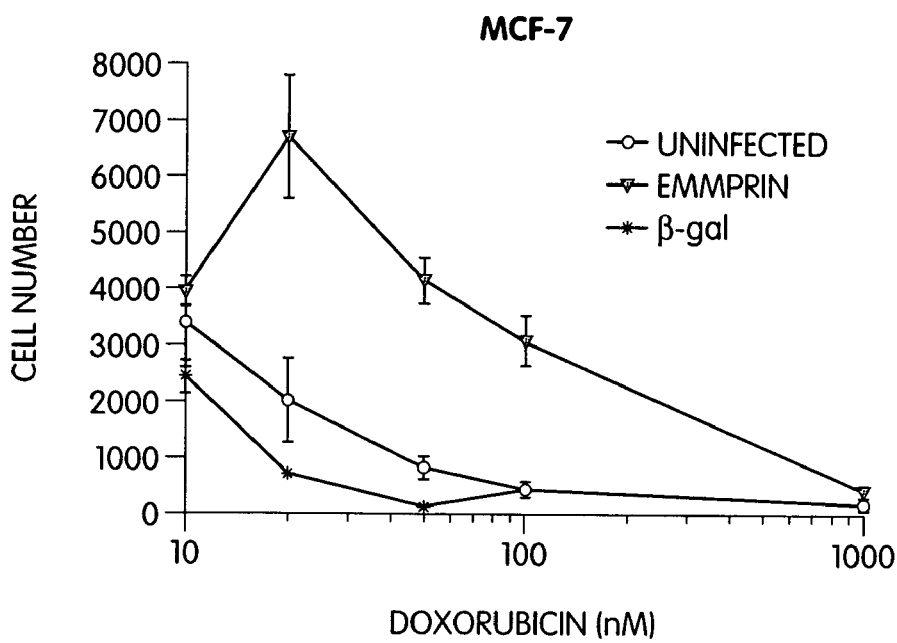
FIG. 16C is a line graph showing doxorubicin response of untreated MCF-7 cells or cells infected overnight with a recombinant emmprin adenovirus or a control β-galactosidase adenovirus (β-gal) that were treated as described in FIG. 16B.
Figure 16D:
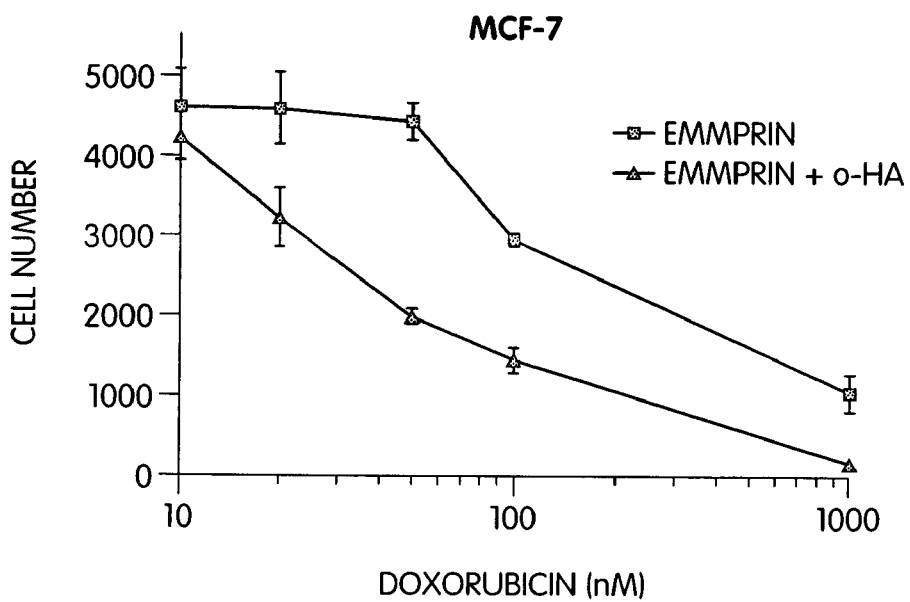
FIG. 16D shows reversal of emmprin-induced drug-resistance in recombinant emmprin adenovirus-infected MCF-7 cells. Emmprin adenovirus-infected MCF-7 cells or control β-galactosidase adenovirus (β-gal)-infected cells were treated in the presence or absence of 100 μg/ml hyaluronan oligomers (o-HA) as described in FIG. 16B. The results in FIGS. 16A-D are expressed as the means (±S.D) of three independent experiments performed in triplicate.

MCF-7 cells infected with a recombinant emmprin adenovirus were found to be more resistant to doxorubicin treatment than controls (FIG. 16C). Further, this effect was found to be reversed by treatment with hyaluronan oligomers (FIG. 16D).

Example 16

Effect of Hyaluronan Oligomers on PI3/Akt Cell Survival Pathway

Further, hyaluronan oligomers were found to suppress the PI3 kinase/Akt cell survival pathway. One of the downstream effects of this pathway is phosphorylation of BAD, which reverses its pro-apoptotic effects (Datta, S. R., et al. *Genes Dev* 13, 2905-27, 1999). Hyaluronan oligomers inhibit BAD phosphorylation at serine 136, the major site phosphorylated by Akt. However these studies were performed in different cells than those used here.

Figure 17A:
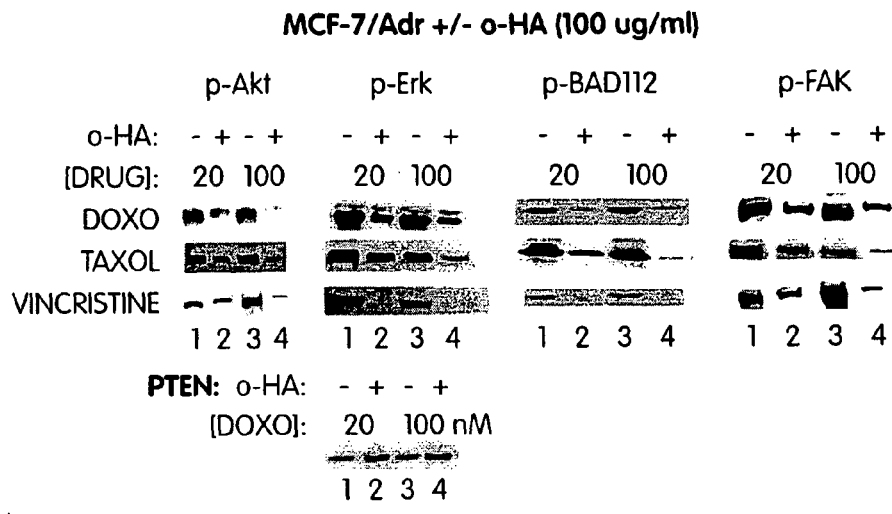
FIG. 17A is a representation of a Western blot of extracts of MCF-7/Adr cells, showing that hyaluronan oligomers regulate cell survival pathways. Cells were treated in the presence of various drugs with and without 100 μg/ml hyaluronan oligomers (o-HA) as in FIG. 15A and Table 1. Cells were processed for Western blot analysis of phosphorylated Akt (p-Akt) and PTEN. Similar results were obtained for PTEN with taxol and vincristine (not shown). Doxorubicin (Doxo): lane 1, 20 nM; lane 2, 20 nM+o-HA; lane 3, 100 nM; lane 4, 100 nM+o-HA. Taxol: lane 1, 20 nM; lane 2, 20 nM+o-HA; lane 3, 100 nM; lane 4 100 nM+o-HA. Vincristine: lane 1, 10 nM; lane 2, 10 nM+o-HA; lane 3, 100 nM; Lane 4, 100 nM+o-HA. Total Akt was not altered in these experiments (not shown).

Therefore, the effects of the hyaluronan oligomers on this pathway was tested in the MCF-7/Adr cells. It was found that hyaluronan oligomers suppressed phosphorylation of Akt and stimulated expression of PTEN in the presence of the various drugs, i.e. doxorubicin, taxol, vincristine (FIG. 17A) and BCNU. PI3 kinase activity was also inhibited, and no effects were observed on total levels of Akt. These effects would be expected to lead to decreased phosphorylation of BAD. However, in MCF-7/Adr cells as opposed to the cells used previously (HCT116 human colon carcinoma and TA3/St mouse mammary carcinoma), very little phosphorylation of BAD at serine 136 was found in the presence or absence of the drugs and oligomers. For this reason, further work addressed the MAP kinase pathway, which also leads to BAD phosphorylation, in this case at serine 112 (Bonni, A., et al., *Science* 286, 1358-62, 1999; Mabuchi, S., et al., *J Biol Chem* 277, 33490-500, 2002; Baumgartner, G., et al. *Cancer Lett* 131, 85-99, 1998).

Figure 17B:
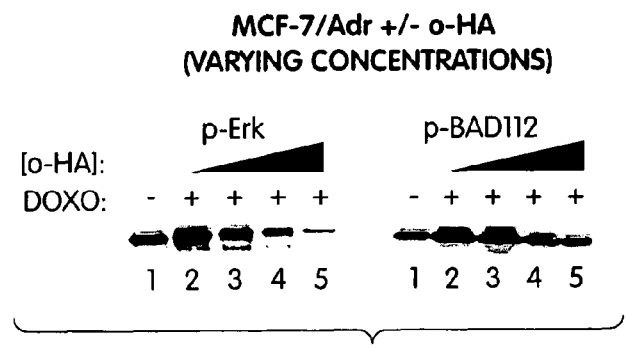
FIG. 17B is a representation of a Western blot of extracts of MCF-7/Adr cells that were treated as in A and processed for Western blotting of p-Erk and p-BAD112 (lane numbers as in A). Similar results were obtained with p-Raf-1 but no changes in total levels of Raf-1 were observed (not shown).
Figure 17C:
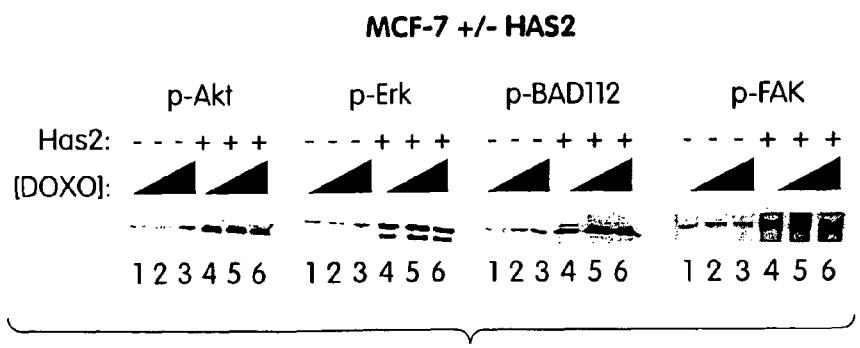
FIG. 17C is a representation of MCF-7 cells that were infected with recombinant adenovirus carrying Has2 or α-galactosidase adenovirus and were processed for Western blot analysis of p-Akt, p-Erk, p-BAD12, and p-FAK. Lane 1-3, β-galactosidase; lanes 4-6, Has2. Lanes 1 and 4, no addition; lanes 2 and 5, 20 nM doxorubicin; lanes 3 and 6, 100 nM doxorubicin.

The data herein show strong phosphorylation of BAD at serine 112 in the MCF-7/Adr cells treated with the various drugs. These results imply that the MAP kinase pathway is more involved in phosphorylating BAD than the PI3 kinase pathway in these cells. The data also showed that this phosphorylation is inhibited by hyaluronan oligomers (FIG. 17B, 17C). In addition the oligomers inhibit phosphorylation, but not total levels, of upstream components of this pathway, i.e. Erk (FIG. 17B, 17C) and Raf-1, in the presence of the various drugs.

Since these experiments were done under anchorage-dependent culture conditions, the MAP kinase pathway might be activated by FAK (Tamura, M. et al., *J Natl Cancer Inst* 91, 1820-8, 1999; Almeida, E. A. et al., *J Cell Biol* 149, 741-54, 2000). Therefore FAK phosphorylation was examined in drug-treated MCF-7/Adr cells in the presence and absence of hyaluronan oligomers, and to determine whether the oligomers inhibit phosphorylation of FAK. Inhibition of p-Erk, p-BAD112, and p-FAK levels in these experiments was found to vary from 50-90%, depending on drug and oligomer dosage. Many of these experiments were also performed with 50-1000 nM concentration of BCNU, and similar inhibition was observed.

Since increased hyaluronan production causes enhanced drug resistance in MCF-7 cells it was also determined whether these pathways were stimulated in recombinant Has2 adenovirus-infected cells. Phosphorylation of Akt, Erk, BAD112, and FAK was found to be increased in drug-treated, HAS2 adenovirus-infected cells compared to controls, whereas PTEN expression was decreased.

The examples above indicate that endogenous hyaluronan-tumor cell interactions are a crucial component of regulation of multi-drug resistance in cancer cells, and that the most likely mechanism whereby hyaluronan acts is by stimulating the PI3 kinase and MAP kinase cell survival pathways, leading to various anti-apoptotic consequences such as BAD phosphorylation. Active, non-phosphorylated BAD interacts with pro-survival Bcl-2 family members and induces apoptosis (Datta, S. R., et al., *Genes Dev* 13, 2905-27, 1999). BAD is inactivated by phosphorylation at serine 136 by Akt or at serine 112 by Erk, either of which leads to anti-apoptotic consequences that can result in increased drug resistance in tumor cells (Bonni, A., et al., *Science* 286, 1358-62, 1999; Mabuchi, S., et al., *J Biol Chem* 277, 33490-500, 2002; Baumgartner, G., et al., *Cancer Lett* 131, 85-99, 1998). In the MCF-7/Adr human mammary carcinoma cells used here, regulation of BAD phosphorylation is mediated mainly by Erk. However, in HCT116 human colon carcinoma and TA3/St mouse mammary carcinoma cells, phosphorylation of BAD by Akt is prominent. In either case, treatment of the cells with hyaluronan oligomers is inhibits this process, and promotes apoptosis of the cancer cells.

Data herein not only document a role for hyaluronan in multi-drug resistance, they also indicate that perturbation of hyaluronan interactions sensitizes resistant cells. Thus, such perturbations may provide a dual therapeutic role since they have an intrinsic effect on tumor growth and metastasis as well as sensitizing cancer cells to chemotherapeutic agents, as shown herein.

The data herein show that treatment of multi-drug resistant cells with hyaluronan oligomers sensitizes them to drug treatment. The adriamycin-resistant cell line MCF-7/Adr, cells of which were made resistant to doxorubicin, were found to become sensitized to each of the following drugs, by the extent indicated: sensitized to doxorubicin by 55-fold, sensitized to BCNU by 78-fold, sensitized to taxol by 12-fold, and sensitized to vincristine by 10-fold. Further, cells of the cell line MDA MB231 were found to become sensitized to methotrexate by 133-fold as a result of treatment with hyaluronan oligomers. No significant effect was observed from treatment with hyaluronan oligomers of drug sensitive MCF-7 cells.

Effects of level of endogenous hyaluronan synthesis in cells was also examined, by providing up-regulation of hyaluronan synthase (using recombinant adenovirus). As a result of such up-regulation, cells that are drug-sensitive, MCF-7, were found to become 12-fold more resistant, and this effect was found to be reversed by HA oligomer treatment.

Up-regulation of emmprin, a protein that is a member of the Ig superfamily, and which is found to be enriched on the surfaces of most malignant cancer cells, was found to stimulate hylauronan synthesis. As a result of such up-regulation, the MCF-7 cells were found to become 10-15-fold more drug resistant, and this effect was found to be reversed by HA oligomer treatment.

The anti-tumor drugs were found to stimulate the following pathways: PI3 kinase/Akt; Raf/Erk; and FAK, which pathways are involved in cell survival signaling. Further, it was found that treatment with HA oligomers suppressed these pathways in the presence or absence of the drugs. Up-regulation of synthesis pf hyaluronan or emmprin had the opposite effect, i.e. stimulated these pathways.

Without being limited by any particular mechanism or intracellular mode of action, these data demonstrate that treatment of cells with HA oligomers inhibits the effects of endogenous hyaluronan synthesis, so that anti-cancer therapeutic agents which are pro-apoptotic drugs have a greater opportunity to produce death of a tumor cell in an otherwise drug-resistant cell.

Example 17

Figure 18B:
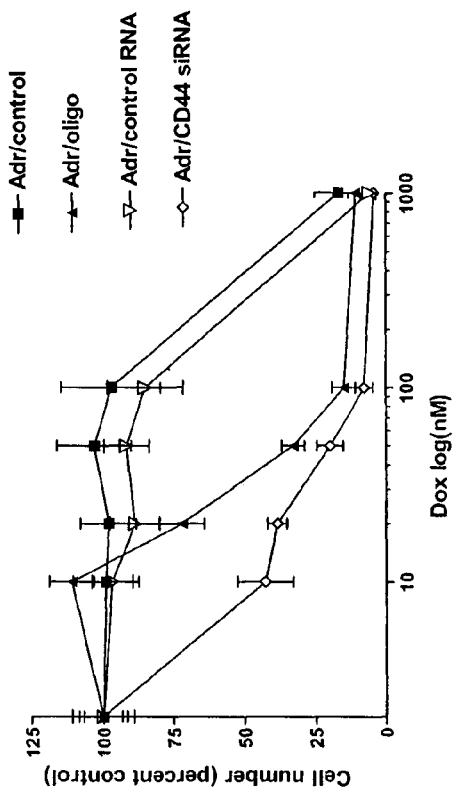
FIG. 18B shows drug resistance of cells cells (solid squares), inhibited resistance of these cells treated with 100 μg/ml HA oligomers (solid triangles), inhibited resistance of these cells treated with siRNA encoding CD44 (open diamonds), and drug resistance of these cells treated control RNA having a scrambled nucleotide sequence.
Figure 18A:
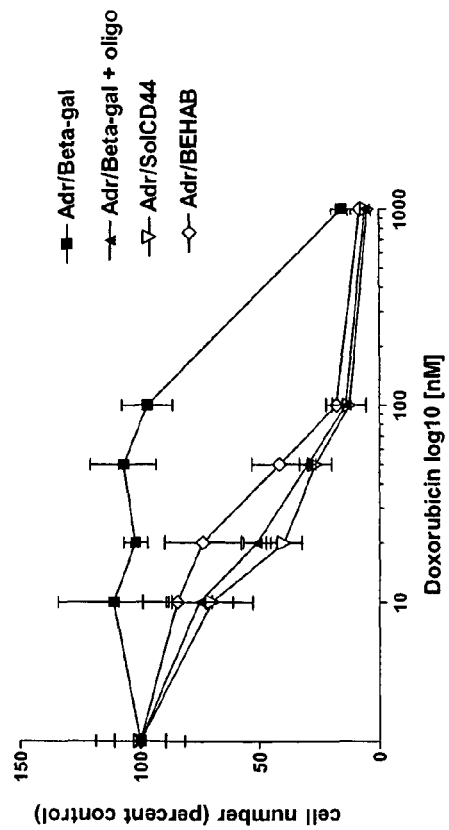
FIG. 18A shows drug resistance of recombinant cells infected with adenovirus carrying β-galactosidase (solid squares), inhibited resistance of these cells treated with 100 μg/ml HA oligomers (solid triangles), inhibited resistance of recombinant cells infected with adenovirus carrying soluble CD44 (inverted open triangles), and inhibited resistance of recombinant cells infected with adenovirus carrying a link module which is a soluble hyaluronan link module (open diamonds).

Effect of Hyaluronan-Binding Decoys and Down Regulation of CD44 on Doxorubicin Resistance of MCF-7/Adr Cells The established system described above for study of drug resistance, i.e. MCF-7/Adr human mammary carcinoma cells that have been selected for resistance to doxorubicin (Fairchild, C. R., et al., *Cancer Res* 47, 5141-8, 1987) was here further used to analyze the effect of hyaluronan-binding decoys (FIG. 18A), and an agent that down regulates expression of the receptor for hyaluronan-binding, CD44, siRNA having a nucleotide sequence complementary to a sequence for RNA transcribed from the CD44 gene (FIGS. 18A and 18B).

Figure 15A:
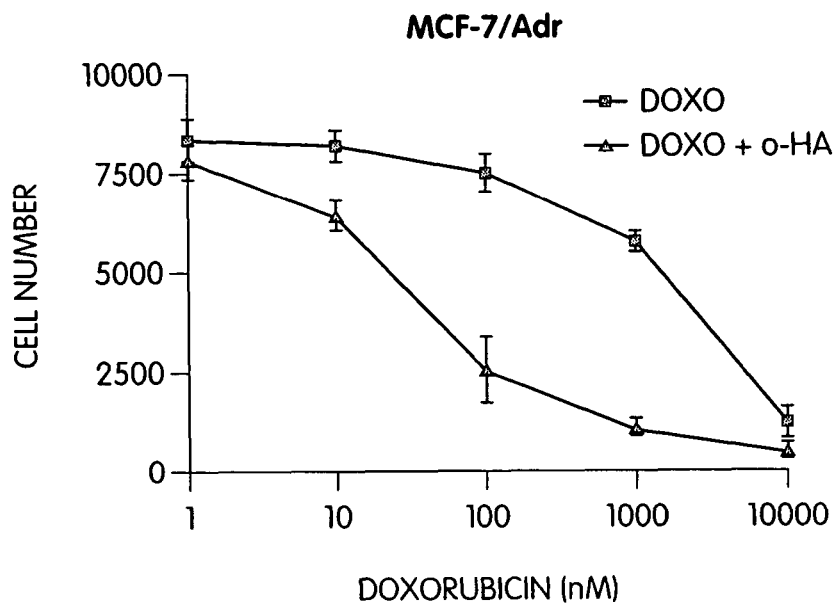
FIG. 15A is a line graph showing that MCF-7/Adr drug-resistant human mammary carcinoma cells grown in culture with hyaluronan oligomers are sensitized to doxorubicin. MCF-7/Adr cells were obtained from MCF-7 cells by being selected for drug resistance by exposure to doxorubicin. Cells were grown for 24 h in 24-well plates in RPMI 1640 medium containing Glutamex 1 plus 10% fetal bovine serum at 37° in 5% $CO_2$. Various concentrations of doxorubicin (doxo) were then added and the cells incubated for another 72 h, followed by a further 24 h in the presence or absence of 100 μg/ml hyaluronan oligomers (o-HA). The oligomers were a mixed population of 3-8 repeating disaccharides in length. The cells were then harvested and the number of viable cells was determined in a Coulter Counter.
Figure 15B:
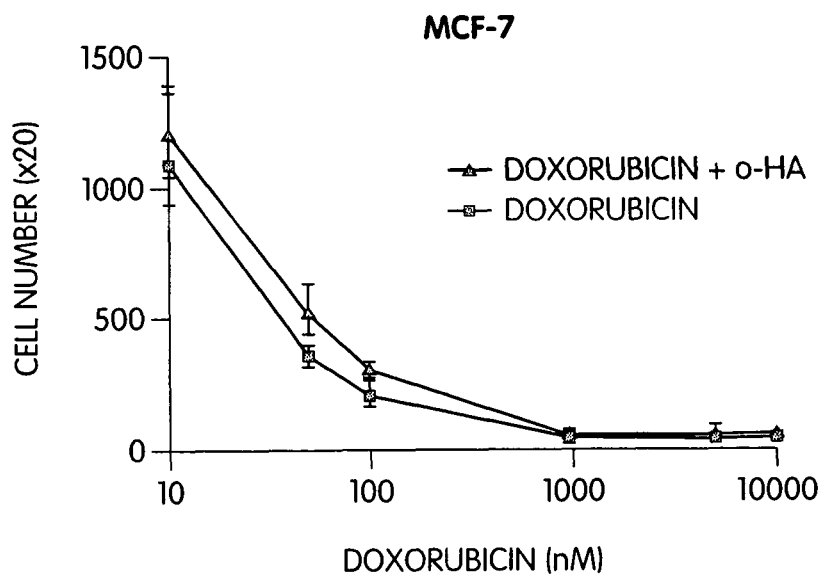
FIG. 15B is a line graph showing that MCF-7 human mammary carcinoma cells are more sensitive to doxorubicin than MCF-7/Adr cells, and that -HA treatment does not significantly sensitize MCF-7 cells.

It is shown above that 100 µg/ml hyaluronan oligomers caused ~55-fold sensitization of the MCF-7/Adr cells to the drug, and had little effect on the already sensitive MCF-7 cells (FIGS. 15A, 15B; Table 1). Doxorubicin resistance in these cells was further shown to be reversed by soluble CD44 (FIG. 18A), which is a hyaluronan-binding decoy, and by a binding protein specific for hyaluronan (HA-binding link module construct or BEHAB), each of which was introduced into these cells by infection with an adenovirus carrying the gene encoding these decoys. The extent of these effects were similar to inhibition of drug resistance found by treating cells with o-HA, also shown in FIG. 18A.

Similar results were obtained with siRNA specfic for expression of the CD44 protein which is a receptor for HA binding and therefore also an HA decoy. The extent of the effect was even greater than that found with treatment of cells with o-HA.

It is anticipated that HA mimetics, such as peptides that mimic the structure of HA oligomers (Ziebell et al., Chem Biol 8(11): 1081-1094, 2001), can function similarly to inhibit drug resistance and restore drug sensitivity.

Example 18

Hyaluronan Regulation of MDR Transporter Expression

Expression of two proteins discussed in Example 8 above involved in multiple drug resistant transport, MDR1 and MRP2, was investigated for possible response to hyaluronan.

Figure 19:
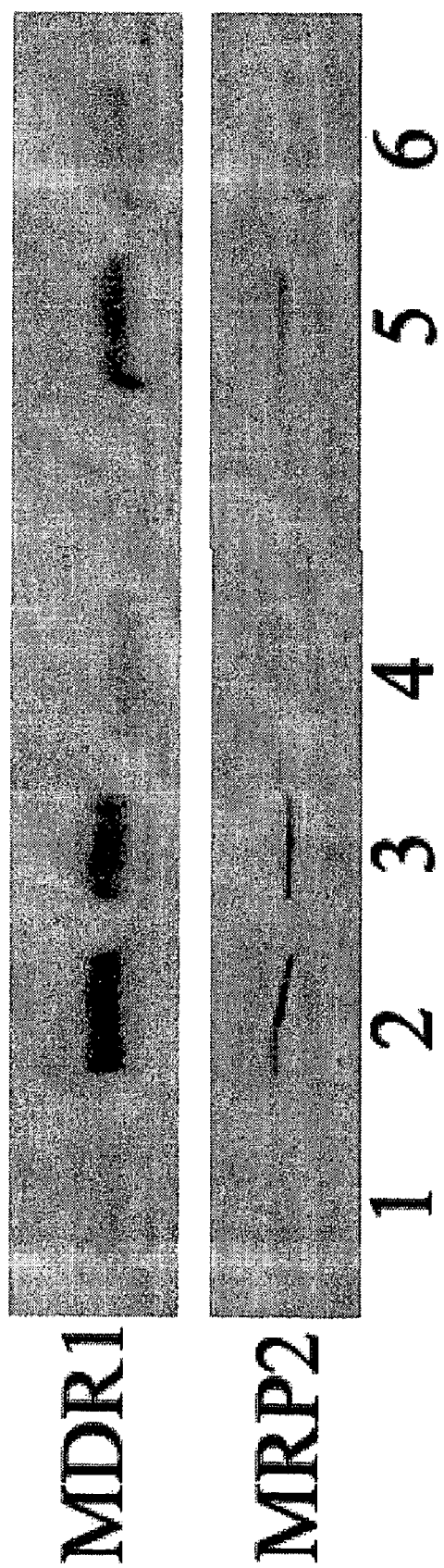
FIG. 19 is a set of photographs of a Western blot of MDR-1 and MRP2 in extracts of MCF-7 cells that were treated as follows: control (lane 1); infected with recombinant adenovirus carrying Has2 (lane 2); infected with recombinant adenovirus carrying Emmprin (lane 3); same cells as in lane 4 treated with HA oligomers (lane 4); MCF-7/Adr cells as in FIG. 17 (lane 5); and cells as in lane 5 treated with HA oligomers (lane 6).

FIG. 19 shows that for both proteins, agents known to affect extent or inhibition of drug resistance reduce expression of both MDR1 and MRP2, and in general, level of resistance correlates with the intensity of the band of each of these proteins. These bands are more prominent in control cells of cell line MCF-7/Adr (lane 6) than in control cells of parent cell line MCF-7 (lane 1). Further, treatment of cells with o-HA (lanes 6 and 4 for these respective cell lines) reduces expression. These proteins are associated with mechanisms of efflux of drugs from cells. Without being limited by any particular mechanism of action, these data show that treatment of cells with o-HA restores drug sensitivity by down regulating membrane proteins involved in drug efflux.

Example 19

Measuring Transport of Drugs in Cells and Cell Vesicles

Figure 20A:
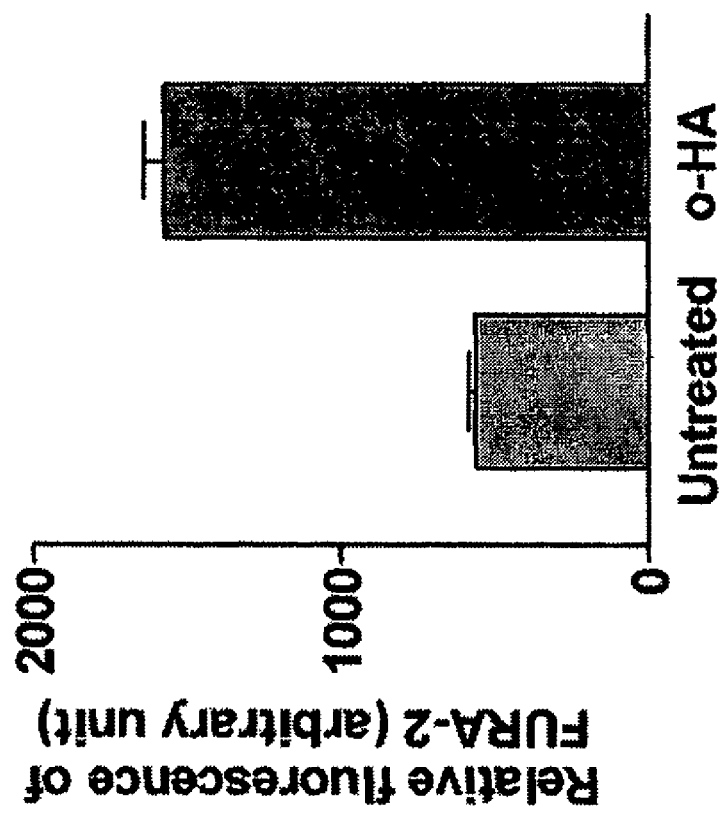
FIG. 20A is a bar graph showing relative fluorescence of FURA-2 in MCG-7/Adr whole cells pre-incubated in the presence or absence of HA oligomers (100 μg/ml).

To determine whether hyaluronan oligomers inhibit drug transport, analysis was performed by direct measurement of transport of fluorescent compound Fura-2 (which is an acronym for the commercially available compound 1-[6-Amino-2-(5-carboxy-2-oxazolyl)-5-benzofuranyloxy]-2-(2-amino-5-methylphenoxy)ethane-N,N,N',N'-tetraacetic acid, pentapotassium salt) into MCF-7/Adr cells, as shown in FIG. 20A. The data show that o-HA treated cells accumulate more than twice the FURA-2, indicate that efflux is reduced in the treated cells, compared to control untreated cells.

This result with whole cells was further tested by preparing membrane vesicles in each of two orientations: inside-out (indicated I-O) and inside-in, i.e., right side in, indicated I-I). With this system, efflux would be seen as accumulation into vesicles with the I-O orientation, and not into vesicles with the I-I orientation. This prediction is confirmed by data shown in FIG. 20B, i.e., compare accumulation in lanes 3 and 4). Further, the data confirm in FIG. 20B that o-HA treatment reduces the efflux, i.e., reduces accumulation of $^{14}$C-doxorubicin into the I-O oriented vesicles (compare lanes 4-5 with treated vesicles in lane 6). The extent of efflux is also consistent with the phenotype of the two cell lines: the drug-resistant strain MCF-7/Adr (lane 4) shows greater drug efflux than the sensitive parent cell line MCF-7 (lane 2). However in the inside-in (I-I) orientations (lanes 1 and 3) essentially no transport is observed and the two cell lines are indistinguishable.

Figures 20B, 20C:
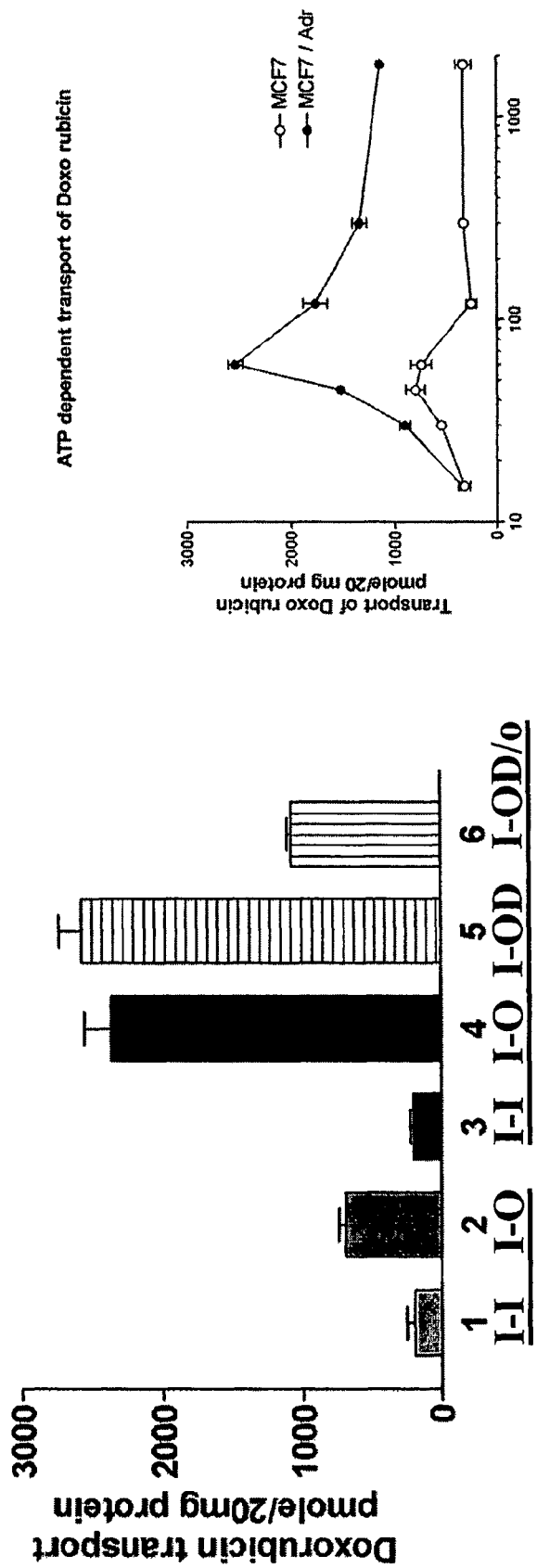
FIG. 20B is a bar graph showing inhibition of $^{14}C$-doxoribicin transport (on the ordinate, in pmole/20 mg protein) into inverted (I-O, inside-out) but not inside-in (I-I) membrane vesicles in MCF-7 and MCF-7/Adr cells, with each bar as follows: bar 1, MCF-7 I-I vesicles; bar 2, MCF-7 I-O vesicles; bar 3, MCF-7/Adr I-I vesicles; bar 4, MCF-7/Adr I-O vesicles; bar 5, MCF-7/Adr I-O vesicles, from cells pre-treated with 50 nM doxorubicin; and bar 6, MCF-7/Adr I-O vesicles, from cells pre-treated with 50 nM doxorubicin and HA oligomers. Following pre-treatment, membranes were incubated with $^{14}C$-doxoribicin for 60 seconds.
FIG. 20C is a line graph of $^{14}C$-doxoribicin transport shown on the ordinate as in FIG. 20B, into MCF-7 and into MCF-7/Adr I-O vesicles, as a function of time in seconds, on the abscissa, in the presence of ATP (background values in absence of ATP were subtracted from the data shown). These data show that membranes from MCF-7 cells are less efficient than MCF-7/Adr cells at transporting the drug at all times. A time point of 60 seconds was chosen for use in data obtained in FIG. 20B.

FIG. 20C shows that efflux from I-O vesicles as a function of time, with a peak of efflux followed by a plateau is reached. These data are consistent in both cell lines, with the parent cell line showing reduced levels of efflux at all time points.

Additional embodiments of the invention can be found in the following claims, which are not to be construed as further limiting.

What is claimed is:

1. A pharmaceutical composition for treating a multi-drug resistant cell, the composition comprising a small hyaluronan oligomer as an active agent for modulation of anti-apoptotic pathways and multidrug resistant transporter expression and/or function wherein the oligomer is present in an effective dose for reducing resistance by at least about ten fold of the cell to a drug, wherein the drug is an anti-cancer agent, the composition further comprising the anti-cancer agent.

2. A pharmaceutical composition for treating a multi-drug resistant cell, the composition comprising a small hyaluronan oligomer as an active agent for modulation of anti-apoptotic pathways and multidrug resistant transporter expression and/or function wherein the oligomer is present in an effective dose for reducing resistance by at least about ten fold of the cell to a drug, the composition further comprising an additional therapeutic agent.

3. A pharmaceutical composition for treating a multi-drug resistant cell, the composition comprising a small hyaluronan oligomer as an active agent for modulation of anti-apoptotic pathways and multidrug resistant transporter expression and/or function wherein the oligomer is present in an effective dose for reducing resistance by at least about ten fold of the cell to a drug wherein the effective dose is 5 mg/kg body weight.

4. The composition of claim 2, further comprising a pharmaceutically acceptable excipient.

5. The composition of claim 2, wherein the additional therapeutic agent is an anti-infective agent.

6. The composition of claim 2, wherein the additional therapeutic agent is a hematopoietic or erythropoietic agent.

7. The composition of claim 2, wherein the additional therapeutic agent is an inhibitor of multi-drug resistance.

8. The pharmaceutical composition of claim 7, wherein the inhibitor is a tamoxifen.

9. A pharmaceutical composition for treating a multi-drug resistant cell, the composition comprising a small hyaluronan oligomer as an active agent for modulation of anti-apoptotic pathways and multidrug resistant transporter expression and/or function wherein the oligomer is present in an effective dose for reducing resistance by at least about ten fold of the cell to a drug, wherein the small hyaluronan oligomer is a hyaluronan receptor ligand or modulator, the composition further comprising an siRNA that inhibits expression of the receptor.

10. A pharmaceutical composition for treating a multi-drug resistant cell, the composition comprising a small hyaluronan oligomer as an active agent for modulation of anti-apoptotic pathways and multidrug resistant transporter expression and/or function wherein the oligomer is present in an effective dose for reducing resistance by at least about ten fold of the cell to a drug, the composition further comprising an antibody that binds with high specificity and affinity to an hyaluronan receptor CD44.

11. The composition according to claim 1, wherein the additional therapeutic agent is at least one anti-cancer agent selected from the group consisting of: adriamycin, methotrexate, cisplatin, paclitaxel, docetaxel, doxorubicin, vinblastine, vincristine, BCNU, camptosar, 5-flurouracil, Velcade, fluorouracil, ZD0473, Gleevec, and oncovine.

12. The composition according to claim 1, wherein the cancer is selected from the group consisting of: melanoma; colon carcinoma; pancreatic; lymphoma; leukemia; glioma; lung; esophagus; mammary; prostate; head and neck; ovarian; kidney; and liver cancer.

13. The composition of claim 2, wherein the oligomer contains at least 3 disaccharide subunits.

14. The composition of claim 2, wherein the oligomer contains at least 6 disaccharide subunits.

15. The composition of claim 2, wherein the oligomer contains three to eight repeating disaccharide subunits.

16. The composition of claim 2, wherein the oligomer contains three to ten disaccharide subunits.

17. The composition of claim 2, wherein the oligomer contains less than 200 disaccharide subunits.

18. The composition of claim 2, wherein the hyaluronan oligomer is derivatized.

19. The composition of claim 18, wherein the derivatized hyaluronan oligomer is selected from the group consisting of alkylated, alkoxylated, and reduced.

20. The composition of claim 18, wherein the derivatized hyaluronan oligomer is selected from the group consisting of substituted with a carbodiimide, an N-(2-hydroxypropyl) methacrylamide, an amine, and a hydrazide.

21. The composition of claim 2, wherein the cell is a cancer cell or a bacterial cell.

22. The composition of claim 21, wherein the cell is from the bacterial genus of *Streptococcus*.

* * * * *